US010421985B2

(12) United States Patent
Ronin

(10) Patent No.: US 10,421,985 B2
(45) Date of Patent: Sep. 24, 2019

(54) METHODS FOR PRODUCING SIALYLATED THERAPEUTIC PROTEINS

(71) Applicant: GLYCOTREK, Carry-le-Rouet (FR)

(72) Inventor: Catherine Ronin, Sausset-les-Pins (FR)

(73) Assignee: GLYCOTREK, Carry-le-Rouet (FR)

( * ) Notice: Subject to any disclaimer, the term of this patent is extended or adjusted under 35 U.S.C. 154(b) by 312 days.

(21) Appl. No.: 14/904,342

(22) PCT Filed: Jul. 11, 2014

(86) PCT No.: PCT/EP2014/001904
§ 371 (c)(1),
(2) Date: Jan. 11, 2016

(87) PCT Pub. No.: WO2015/003811
PCT Pub. Date: Jan. 15, 2015

(65) Prior Publication Data
US 2016/0153020 A1    Jun. 2, 2016

(30) Foreign Application Priority Data

Jul. 11, 2013 (EP) .................................. 13003501

(51) Int. Cl.
C12P 21/00 (2006.01)
C12N 9/10 (2006.01)
C07K 14/575 (2006.01)
C07K 16/24 (2006.01)
C12N 15/85 (2006.01)

(52) U.S. Cl.
CPC .......... C12P 21/005 (2013.01); C07K 14/575 (2013.01); C07K 16/241 (2013.01); C12N 9/1048 (2013.01); C12N 9/1051 (2013.01); C12N 9/1081 (2013.01); C12N 15/85 (2013.01); C12P 21/00 (2013.01); C07K 2317/14 (2013.01); C07K 2317/41 (2013.01); C07K 2319/02 (2013.01); C07K 2319/03 (2013.01); C12Y 204/99001 (2013.01)

(58) Field of Classification Search
None
See application file for complete search history.

(56) References Cited

U.S. PATENT DOCUMENTS

| 4,861,719 | A | 8/1989 | Miller |
| 5,225,539 | A | 7/1993 | Winter |
| 5,278,056 | A | 1/1994 | Bank et al. |
| 5,585,089 | A | 12/1996 | Queen et al. |
| 5,641,668 | A * | 6/1997 | Berger ................. C12N 9/1051 435/193 |
| 5,882,877 | A | 3/1999 | Gregory et al. |
| 6,013,516 | A | 1/2000 | Verma et al. |
| 6,127,175 | A | 10/2000 | Vigne et al. |
| 6,464,998 | B1 | 10/2002 | Beuzard et al. |

FOREIGN PATENT DOCUMENTS

| GB | 2 188 638 A | 10/1967 |
| WO | 94/19478 A1 | 9/1994 |
| WO | 95/14785 A1 | 6/1995 |
| WO | 96/22378 A1 | 7/1996 |
| WO | 2005/076013 A2 | 8/2005 |
| WO | 2007/135194 A2 | 11/2007 |
| WO | 2009/127826 A1 | 10/2009 |
| WO | 2012/113863 A1 | 8/2012 |

OTHER PUBLICATIONS

El May N et al.: "Engineering a human-like glycosylation to produce therapeutic glycoproteins based on 6-linked sialylation in CHO cells" In: Apr. 17, 2013 (Apr. 17, 2013), Beck A, "Glycosylation Engineering of Biopharmaceuticals: Methods and Protocols", Methods in Molecular Biology, Humana Press, US, XP009173723, ISSN: 1940-6029 vol. 988, pp. 19-29, DOI: 10.1007/978-1-62703-327-5 2, abstract.

Onitsuka M et al.: "Enhancement of sialylation on humanized IgG-like bispecific antibody by overexpression of α2,6-sialyltransferase derived from Chinese hamster ovary cells", Applied Microbiology and Microbiology, Springer, Berlin, DE, vol . 94, No. I, Dec. 29, 2011 (Dec. 29, 2011), pp. 69-80, XP035029858, ISSN: 1432-0614, DOI: 10.1007/500253-011-3814-1 abstract, materials and methods; results; discussion.

International Search Report, dated Nov. 12, 2014, from corresponding PCT application.

* cited by examiner

Primary Examiner — Anand U Desai
(74) Attorney, Agent, or Firm — Young & Thompson

(57) ABSTRACT

The present invention relates to a transformed mammalian cell including a heterologous nucleic acid sequence (i) encoding a polypeptide including the catalytic domain of ST6Gal1 or of ST6Gal2 and, optionally, at least one nucleic acid sequence (ii) encoding a therapeutic protein including at least one glycosylation site, the transformed mammalian cell expressing the therapeutic protein with a sialylation on the at least one glycosylation site.

7 Claims, No Drawings
Specification includes a Sequence Listing.

METHODS FOR PRODUCING SIALYLATED THERAPEUTIC PROTEINS

This International patent application claims the priority of European patent application EP 13003501.7 filed on Jul. 11, 2013, which is herein incorporated by reference.

FIELD OF THE INVENTION

The present invention relates to the production of therapeutic protein presenting optimized glycosylation pattern, particularly optimized sialylation.

BACKGROUND OF THE INVENTION

Currently, the majority of newly marketed biotherapeutics consist in recombinant proteins. Nevertheless, an important part of these proteins of human origin are associated to side effects relative to immunogenicity.

Glycosylation and more particularly sialylation are modifications which affect both the production and activity of proteins, and participate to proper recognition of proteins by the immune system. These post-translational modifications are also involved in the solubility, stability, protein-protein and cell-cell interactions as well as in the circulatory life span of proteins.

Thus, there is a crucial need to produce recombinant proteins having a glycosylation and a sialylation pattern as similar as possible to a human native protein for developing proteins for medical use. It is worth noting that at the present time, the vast majority (>75%) of recombinant proteins are produced using mammalian non-human expression systems and many of them display undesired immunogenicity side effects and more than often short half-lives. Particularly, current recombinant proteins are particularly insufficiently sialylated and none contain 6-linked sialic acid, which is the typical mode of glycosylation in human blood It is therefore widely admitted that expression systems used for producing proteins drugs request major improvements to obtain recombinant proteins having a glycosylation and more especially sialylation pattern similar to human native proteins.

SUMMARY OF THE INVENTION

The inventors interestingly showed that the expression of the minimal catalytic domain of the sialyltransferase ST6Gal alone in mammalian cell-culture expression systems permit the production of human proteins having an altered overall glycoprofile and a sialylation pattern of the serum type, contrary to the one which can be obtained by the full length wild type ST6GalI and this even if this minimal catalytic domain is not anchored in the Golgi.

The inventors particularly demonstrated that the expression of said catalytic domain in a mammalian cell permit to significantly improve the sialylation pattern of the in cellulo produced proteins and also to increase the productivity of said producer cells.

Moreover, the inventors established surprisingly that unlike the strict α-1,3 branch specificity sialylation of wild type ST6Gal-I for glycoproteins (BARB et al., *Biochemistry*, vol. 48(41), p: 9705-9707, 2009), said catalytic domain of ST6Gal-I (SEQ ID NO: 1) has the capacity to glycosylate significantly all the antennae of multi-antennary glycans.

Thus, the present invention relates to a transformed mammalian cell comprising:

a heterologous nucleic acid sequence (i) encoding a polypeptide comprising the catalytic domain of the ST6 β-galactosyl α-2,6-sialyltranferase 1 (ST6Gal1) defined by the sequence SEQ ID NO: 1 or, the catalytic domain of the ST6 β-galactosyl α-2,6-sialyltranferase 2 (ST6Gal2) defined by the sequence SEQ ID NO: 43, or a derivative thereof, and optionally, at least one heterologous nucleic acid sequence (ii) encoding a therapeutic protein, the sequence of which therapeutic protein comprises at least one glycosylation site, said transformed mammalian cell expressing the therapeutic protein with a sialylation on said at least one glycosylation site.

Advantageously, said mammalian cell is selected in the group comprising CHO cells, HEK-293 cells, COS cells, NSO cells, PER.C6® cells or SP2O cells.

In a preferred embodiment, said nucleic acid sequence (i) encodes the polypeptide consisting in the sequence SEQ ID NO: 1.

In another preferred embodiment, said nucleic acid sequence (i) encodes a polypeptide comprising or consisting in the sequence SEQ ID NO: 35, SEQ ID NO: 36, SEQ ID NO: 37, SEQ ID NO: 38, or SEQ ID NO: 39.

The present invention further relates to a method for producing a therapeutic protein with sialylation on the at least one glycosylation site of said therapeutic protein, said method comprising the steps of:

a) culturing a transformed mammalian cell as defined previously, and b) purifying the therapeutic protein encoded by the nucleic acid sequence (ii).

Preferably, the method of the invention comprises the step b) of determining the glycosylation pattern of the therapeutic protein obtained in step a) and purifying the therapeutic protein with i) a sialylation on at least 2% of its glycosylation site(s), preferably at least 5% of its glycosylation site(s).

The present invention also relates to the use of a transformed mammalian cell as defined previously for the production of a therapeutic protein comprising at least one glycosylation site with a sialylation on said at least one glycosylation site.

Finally, the present invention further relates to a therapeutic protein which can be obtained by said method and to a composition comprising such a therapeutic protein.

DETAILED DESCRIPTION OF THE INVENTION

The invention aims at providing a humanized expression system for producing therapeutic proteins of interest in mammalian cells, said therapeutic proteins being sialylated.

Thus, a first aspect of the invention concerns a transformed mammalian cell comprising:

a heterologous nucleic acid sequence (i) encoding a polypeptide comprising the catalytic domain of the ST6 β-galactosamide α-2,6-sialyltranferase 1 (ST6Gal1) defined by the sequence SEQ ID NO: 1, the catalytic domain of the ST6 β-galactosamide α-2,6-sialyltranferase 2 (ST6Gal2) defined by the sequence SEQ ID NO: 43, or a derivative thereof, and optionally, at least a heterologous nucleic acid sequence (ii) encoding a therapeutic protein, the sequence of which therapeutic protein comprises at least one glycosylation site, said transformed mammalian cell expressing the therapeutic protein with a sialylation on said at least one glycosylation site.

By "transformed cell" is meant a host cell into which at least one vector (or DNA fragment) of interest is transferred by any means, such as by infection, conjugation, transformation, transfection, electroporation, microinjection, calcium chloride precipitation or liposome-mediated transfer. Methods of cell transformation are well known in the art.

Host cells used for the invention are mammalian cells, preferably CHO (Chinese Hamster Ovary) cells such as CHO K1 (ATCC number CCL-31, CCL-61 or CRL-9618), CHO-DHFR (ATCCCRL-9096), CHO-DXB-11, CHO cells having the ATCC number ATCC CRL 1610 or CHO DG44; HEK293 (Human Embryonic Kidney) such as 293 (ATCC number CRL-1573) or HEK-293.2sus (ATCC number CRL-1573.3); COS cells such as COS-1 (ATCC number CRL-1650) and COS-7 (ATCC number CRL-1651); PER.C6® cells (human retina derived cell lines; DSM BIOLOGICS, CRUCELL); SP2O such as SP2/0-Ag14 cells (ATCC Accession Number CRL-1851), NSO cells, Sp2/0, NS1, BHK, Ag653, P3X63Ag8.653 cells (ATCC Accession Number CRL-1580), BHK21 (e.g., ATCC CRL-10), BSC-1 (e.g., ATCC CRL-26) cells, HepG2 cells, P3X63Ag8.653, 293 cells, HeLa cells, NIH 3T3, NIH 273, and the like, or any cells derived therefrom, including cell fusions of the above, such as to protein producing cells, such as B-cells, antibody producing cells, isolated or cloned spleen or lymph node cells, and the like.

A preferred host cell of the invention is selected among the group comprising said mammalian cells are CHO cells, HEK-293 cells, COS cells, NSO cells, PER.C6® or SP2O cells. More preferably, a host cell of the invention is a CHO cell or a HEK-293 cell.

By "heterologous nucleic acid sequence" is meant a nucleic acid sequence derived from a different organism, species or strain than the one of the host cell. In some aspects, the heterologous nucleic acid sequence is not identical to a wild-type nucleic acid that is found in the same host cell in nature.

According to the invention, the transformed mammalian cell comprises a nucleic acid sequence (i) encoding a polypeptide defined by the sequence SEQ ID NO: 1, by the sequence SEQ ID NO: 43 or a derivative thereof, wherein the sequence SEQ ID NO: 1 corresponds to the minimal catalytic domain of the ST6Gal1 sialyltransferase and SEQ ID NO: 43 corresponds to the minimal catalytic domain of the ST6Gal2 sialyltransferase.

The "ST6Gal1" or "ST6 β-galactosamide α-2,6-sialyltranferase 1" is an enzyme encoded by ST6Gal1 gene, which enzyme is a type II membrane protein catalyzes the transfer of a sialic acid from CMP-sialic acid to galactose containing substrates through a α-2,6 linkage. The ST6Gal1 protein or gene can be from any source, but typically is a mammalian (e.g., human, non-human primate, rodent or bovine/porcine/equine/ovine) ST6Gal1, preferably a human or rodent ST6Gal1. An exemplary native ST6Gal1 amino acid sequence is provided in GenPept database under accession number NP_003023.1 and an exemplary native nucleotide sequence encoding for ST6Gal1 is provided in GenBank database under accession number NM_003032.2. As used herein, the term ST6GAL1 may include naturally occurring ST6Gal1 gene or protein and derivatives thereof.

The "ST6Gal2" or "ST6 β-galactosamide α-2,6-sialyltranferase 2" is an enzyme encoded by ST6Gal2 gene, which enzyme is a type II membrane protein catalyzes the transfer of a sialic acid from CMP-sialic acid to galactose containing substrates through a α-2,6 linkage. The ST6Gal2 protein or gene can be from any source, but typically is a mammalian (e.g., human, non-human primate, rodent or bovine/porcine/equine/ovine) ST6Gal2, preferably a human or rodent ST6Gal2. An exemplary native ST6Gal2 amino acid sequence is provided in GenPept database under accession number NP_001135823 and NP_001135824 for the isoform a and b respectively, which are encoded by the nucleotide sequence provided in GenBank database under accession number NM_001142351 and NM_001142352 respectively. As used herein, the term ST6GAL2 may include naturally occurring ST6Gal2 gene or protein and derivatives thereof.

As used herein, the term "derivative" refers to a nucleic acid or polypeptide having a percentage of identity of at least 85%, preferably at least 90%, more preferably at least 95%, and even more preferably at least 99% with the complete nucleic acid or amino acid sequence of the polypeptide or nucleic acid from which it derives and having the same activity.

As used herein, "percentage of identity" between two amino acids sequences or two nucleic acid sequences, means the percentage of identical amino-acids or nucleic acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids or nucleic acid sequences are usually realized by comparing these sequences that have been previously aligned according to the best alignment; this comparison is realized on segments of comparison in order to identify and compare the local regions of similarity. The best sequences alignment to perform comparison can be realized by using computer softwares using algorithms such as GAP, BESTFIT, BLAST P, BLAST N, FASTA, TFASTA in the Wisconsin Genetics software Package, Genetics Computer Group, 575 Science Dr., Madison, Wis. USA. To get the best local alignment, one can preferably used BLAST software, with the BLOSUM 62 matrix, preferably the PAM 30 matrix. The identity percentage between two sequences of amino acids or nucleic acids is determined by comparing these two sequences optimally aligned, the amino acids sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

In one embodiment of the invention, the nucleic acid sequence (i) consists in a nucleic acid sequence encoding a polypeptide having a length of less than 350 amino acids, preferably a length of less than 300 amino acids.

Preferably, said nucleic acid sequence (i) encodes a polypeptide consisting in the sequence SEQ ID NO: 1, SEQ ID NO: 43 or a derivative thereof.

In another embodiment of the invention, the nucleic acid sequence (i) comprises a nucleic acid sequence encoding the sequence SEQ ID NO: 1, SEQ ID NO: 43 or a derivative thereof.

```
SEQ ID NO: 1    EASFQVWNKDSSSKNLIPRLQKIWKNYLSMNKYKVS
                YKGPGPGIKFSAEALRCHLRDHVNVSMVEVTDFPFN
                TSEWEGYLPKESIRTKAGPWGRCAVVSSAGSLKSSQ
```

|  |  |
|---|---|
|  | LGREIDDHDAVLRFNGAPTANFQQDVGTKTTIRLMN<br>SQLVTTEKRFLKDSLYNEGILIVWDPSVYHSDIPKW<br>YQNPDYNFFNNYKTYRKLHPNQPFYILKPQMPWELW<br>DILQEISPEEIQPNPPSSGMLGIIIMMTLCDQVDIY<br>EFLPSKRKTDVCYYYQKFFDSACTMGAYHPLLYEKN<br>LVKHLNQGTDEDIYLLGKATLPGFRTIHC |
| SEQ ID NO: 43 | RLYSSMSRAFLYRLWKGNVSSKMLNPRLQKAMKDYL<br>TANKHGVRFRGKREAGLSRAQLLCQLRSRARVRTLD<br>GTEAPFSALGWRRLVPAVPLSQLHPRGLRSCAVVMS<br>AGAILNSSLGEEIDSHDAVLRFNSAPTRGYEKDVGN<br>KTTIRIINSQILTNPSHHFIDSSLYKDVILVAWDPA<br>PYSANLNLWYKKPDYNLFTPYIQHRQRNPNQPFYIL<br>HPKFIWQLWDIIQENTKEKIQPNPPSSGFIGILIMM<br>SMCREVHVYEYIPSVRQTELCHYHELYYDAACTLGA<br>YHPLLYEKLLVQRLNMGTQGDLHRKGKVVLPGFQAV<br>HCPAPSPVIPHS |

According to the invention, the nucleic acid sequence (i) may further comprise, in addition to the catalytic domain of ST6Gal1 or ST6Gal2, other domains, such as the cytoplasmic domain, the transmembrane domain, the stem region, or an anchor sequence of a glycosyltransferase, preferably a sialyltransferase, as well as a leader signal sequence of a soluble protein (such as the preprotrypsinogen signal sequence).

As used herein, the term "anchor sequence" of a sialyltransferase refers to a nucleic acid or amino acid sequence comprising the nucleic acid or amino acid sequences of the cytoplasmic domain, the transmembrane domain and the stem region of one or several glycosyltransferases, preferably sialyltransferases.

As used herein, the term "transmembrane domain" (TMD) used above corresponds to a peptide portion composed of a stretch of 17-24 essentially hydrophobic amino acids.

In a particular embodiment, the nucleic acid sequence (i) encodes a secreted polypeptide comprising the catalytic domain of ST6Gal1 or ST6Gal2. Thus, said polypeptide does not comprise any transmembrane domain.

Example of amino acid sequences of transmembrane domains are provided hereafter.

| | |
|---|---|
| SEQ ID NO: 2 | TMD human ST6Gal1:<br>CCVLVFLLFAVICVWKEKKKGSYY |
| SEQ ID NO: 3 | TMD CHO ST6Gal1:<br>YFILAFLLFALICVWKKGSY |
| SEQ ID NO: 4 | TMD mouse ST6Gal1:<br>CFVLVFLLFAIICVWKKGSDY |
| SEQ ID NO: 5 | TMD rat ST6Gal1:<br>LFILVFLLFAVICVWKKGSDY |
| SEQ ID NO: 6 | TMD human ST6Gal 2:<br>MLFGIFAWGLLFLLIFIYFTD |
| SEQ ID NO: 7 | TMD CHO ST6Gal2:<br>MLFGIFVWGLLFLAIFIYFTN |
| SEQ ID NO: 8 | TMD mouse ST6Gal2:<br>MLFGIFVWGLLFLAIFIYFTN |
| SEQ ID NO: 9 | TMD rat ST6Gal2:<br>MLFAIFVWGLLFLAIFIYFTN |
| SEQ ID NO: 10 | TMD human ST3Gal3:<br>NLLLALCLFLVLGFLYYSAW |
| SEQ ID NO: 11 | TMD CHO ST3Gal3:<br>NLLLALCLFLVLGFLYYSAW |
| SEQ ID NO: 12 | TMD mouse ST3Gal3:<br>NLLLALCLFLVLGFLYYSAW |
| SEQ ID NO: 13 | TMD rat ST3Gal3:<br>NLLLALCLFLVLGFLYYSAW |
| SEQ ID NO: 14 | TMD human ST8Sia4:<br>WTICTISLLLIFY |
| SEQ ID NO: 15 | TMD mouse ST8Sia4:<br>WTICTISLLLIFY |
| SEQ ID NO: 16 | TMD rat ST8Sia4:<br>WTICTISLLLIFY |

As used herein, the term "stem region" (SR) used above corresponds to a stretch of at most 246 amino acids downstream the TMD and upstream from the CD.

Examples of amino acid sequences of the stem region is provided thereafter.

| | |
|---|---|
| SEQ ID NO: 17 | DSFKLQTKEFQVLKSLGKLAMGSDSQSVSSSSTQDP<br>HRGRQTLGSLRGLAKAKP |
| SEQ ID NO: 18 | EALKLQAKEFQVTRSLEKLAMRSGSQSMSSSSKQDP<br>KQDSQVLSHARVTAKVKP |
| SEQ ID NO: 19 | EALTLQAKVFQMPKSQEKVAVGPAPAVFSNSKQDPK<br>EGVQILSYPRVTAKVKP |
| SEQ ID NO: 20 | EALTLQAKEFQMPKSQEKVAMGSASQVVFSNSKQDP<br>KEDIPILSYHRVTAKVKP |
| SEQ ID NO: 21 | SNPAEPVPSSLSFLETRRLLPVQGKQRAIMGAAHEP<br>SPPGGLDARQALPRAHP |
| SEQ ID NO: 22 | SNPASPVPSSFSFVENRGLLPVQGKQRAIMGALQES<br>SLPRSLEASKALPGSHP |
| SEQ ID NO: 23 | SNPAAPMPSSFSFLESRGLLPLQGKQRVIMGALQEP<br>SLPRSLDASKVLLDSHP |
| SEQ ID NO: 24 | SNPAAPMPSSFSFLESRGLLPVQGKQRVIMGALQEP<br>SLPRSLEPSKVLMDGHS |
| SEQ ID NO: 25 | KLHLLQWEEDSNSVVLSF |
| SEQ ID NO: 26 | KLHLLQWEDSNSLLLSL |
| SEQ ID NO: 27 | KLHLLQWEDSNSLLLSL |
| SEQ ID NO: 28 | KLHLLQWEDSNSLILSL |
| SEQ ID NO: 29 | KTKEIARTEEHQETQLIGDGELSLSRSLVNSSDKII<br>RKAGSSIFQHN |
| SEQ ID NO: 30 | KTKEIARTEEHQETQLIGDGELCLSRSLVNSSDKII<br>RKAGSTIFQHS |
| SEQ ID NO: 31 | KTKEIARTEEHQETQLIGDGELCLSRSLVNNSDKIT<br>RKAGSTIFQHS |
| SEQ ID NO: 32 | DISEIEEEIGNSGGRGTIRSAVNSLHSKSNRAEVVI<br>NGSSSPAVVDRSNESIKHNI |
| SEQ ID NO: 33 | DISEIEEEIGNSGGRGTIRSAVNSLHSKSNRAEVVI<br>NGSSPPAVADRSNESLKHNI |
| SEQ ID NO: 34 | DISEIEEEIGNSGGRGTIRSAVNSLHSKSNRAEVVI<br>NGSSLPAVADRSNESLKHSI |

According to the invention, the different domains of sialyltransferases comprised in the nucleic acid sequence (i) may derive from different glycosyltransferases, particularly sialyltransferases chosen among the group comprising, but not limited to, ST6Gal1, ST6Gal2, ST3Gal3, ST8Sia2, and ST8Sia4.

The term "ST3Gal3 protein", also known as "ST3 β-galactoside α-2,3-sialyltransferase" is well known in the art and refers to a sialyltransferase encoded in human by the ST3Gal3 gene. The ST3Gal3 protein or gene can be from any source, but typically is a mammalian (e.g., human and non-human primate, including, but not limited to rodent, bovine, porcine, equine and ovine) ST3Gal3, preferably a human ST3Gal3. An exemplary native ST3Gal3 amino acid sequence is provided in GenPept database under accession number NP_001257388.1 and an exemplary native nucleotide sequence encoding for ST3Gal3 is provided in GenBank database under accession number NM_001270459.1. As used herein, the term ST3Gal3 may include naturally occurring ST3Gal3 gene or protein and derivatives thereof.

The term "ST8Sia2 protein", also known as "α-2,8-sialyltransferase 8B" is well known in the art and refers to a sialyltransferase encoded in human by the ST8Sia2 gene. The ST8Sia2 protein or gene can be from any source, but typically is a mammalian (e.g., human and non-human primate including, but not limited to rodent, bovine, porcine, equine and ovine) ST8Sia2, preferably a human ST8Sia2. An exemplary native ST8Sia2 amino acid sequence is provided in GenPept database under accession number NP_006002.1 and an exemplary native nucleotide sequence encoding for ST8Sia2 is provided in GenBank database under accession number NM_006011.3. As used herein, the term ST8Sia2 may include naturally occurring ST8Sia2 gene or protein and derivatives thereof.

The term "ST8Sia4 protein", also known as "α-N-acetylneuraminide α-2,8-sialyltransferase 4" is well known in the art and refers to a sialyltransferase encoded in human by the ST8Sia4 gene. The ST8Sia4 protein or gene can be from any source, but typically is a mammalian (e.g., human and non-human primate including, but not limited to rodent, bovine, porcine, equine and ovine) ST8Sia4, preferably a human ST8Sia4. An exemplary native ST8Sia4 amino acid sequence is provided in GenPept database under accession number NP_005659.1 and an exemplary native nucleotide sequence encoding for ST8Si42 is provided in GenBank database under accession number NM_005668.5. As used herein, the term ST8Sia4 may include naturally occurring ST8Sia4 gene or protein and derivatives thereof.

In a particular embodiment of the invention, the nucleic acid sequence (i) encodes a polypeptide comprising or consisting in the sequence SEQ ID NO: 35.

```
SEQ ID NO: 35 MIHTNLKKKFSYFILAFLLFALICVWKKGSYEALKLQ
              AKEFQVTRSLEKLAMRSGSQSMSSSSKQDPKQDSQVL
              SHARVTAKVKPEASFQVWNKDSSSKNLIPRLQKIWKN
              YLSMNKYKVSYKGPGPGIKFSAEALRCHLRDHVNVS
              MVEVTDFPFNTSEWEGYLPKESIRTKAGPWGRCAVV
              SSAGSLKSSQLGREIDDHDAVLRFNGAPTANFQQDV
              GTKTTIRLMNSQLVTTEKRFLKDSLYNEGILIVWDP
              SVYHSDIPKWYQNPDYNFFNNYKTYRKLHPNQPFYI
              LKPQMPWELWDILQEISPEEIQPNPPSSGMLGIIIM
              MTLCDQVDIYEFLPSKRKTDVCYYYQKFFDSACTMG
              AYHPLLYEKNLVKHLNQGTDEDIYLLGKATLPGFR
              TIHC
```

This sequence SEQ ID NO: 35 consists in an amino acid sequence corresponding to a chimeric peptide comprising the anchor sequence of the ST6Gal1 protein of CHO cells fused to the catalytic domain of the human ST6Gal1 protein.

In another particular embodiment of the invention, the nucleic acid sequence (i) encodes a polypeptide comprising or consisting in the sequence SEQ ID NO: 36.

```
SEQ ID NO: 36 MDYKDDDDKQLQFRSWMLAALTLLVVFLIFADISEIE
              EEIGNSGGRGTIRSAVNSLHSKSNRAEVVINGSSSPAV
              VDRSNESIKHNIKLEASFQVWNKDSSSKNLIPRLQKIW
              KNYLSMNKYKVSYKGPGPGIKFSAEALRCHLRDHVNVS
              MVEVTDFPFNTSEWEGYLPKESIRTKAGPWGRCAVVSS
              AGSLKSSQLGREIDDHDAVLRFNGAPTANFQQDVGTKT
              TIRLMNSQLVTTEKRFLKDSLYNEGILIVWDPSVYHSD
              IPKWYQNPDYNFFNNYKTYRKLHPNQPFYILKPQMPWE
              LWDILQEISPEEIQPNPPSSGMLGIIIMMTLCDQVDIY
              EFLPSKRKTDVCYYYQKFFDSACTMGAYHPLLYEKNL
              VKHLNQGTDEDIYLLGKATLPGFRTIHC
```

This sequence SEQ ID NO: 36 consists in an amino acid sequence corresponding to a chimeric peptide comprising a Flag-Tag, the anchor sequence of the human ST8Sia2 fused to the catalytic domain of the human ST6Gal1 protein.

In still another particular embodiment of the invention, the nucleic acid sequence (i) encodes a polypeptide comprising or consisting in the sequence SEQ ID NO: 37.

```
SEQ ID NO: 37 MSALLILALVGAAVADYKDDDDKQLQFRSWMLAALTLL
              VVFLIFADISEIEEEIGNSGGRGTIRSAVNSLHSKSNR
              AEVVINGSSSPAVVDRSNESIKHNIKLEASFQVWNKDS
              SSKNLIPRLQKIWKNYLSMNKYKVSYKGPGPGIKFSAE
              ALRCHLRDHVNVSMVEVTDFPFNTSEWEGYLPKESIRT
              KAGPWGRCAVVSSAGSLKSSQLGREIDDHDAVLRFNGA
              PTANFQQDVGTKTTIRLMNSQLVTTEKRFLKDSLYNEG
              ILIVWDPSVYHSDIPKWYQNPDYNFFNNYKTYRKLHPN
              QPFYILKPQMPWELWDILQEISPEEIQPNPPSSGMLGI
              IIMMTLCDQVDIYEFLPSKRKTDVCYYYQKFFDSACTM
              GAYHPLLYEKNLVKHLNQGTDEDIYLLGKATLPGFRTI
              HC
```

This sequence SEQ ID NO: 37 consists in an amino acid sequence corresponding to a chimeric peptide comprising a preprotrypsinogen signal sequence, a Flag-Tag, the anchor sequence of the human ST8Sia2 fused to the catalytic domain of the human ST6Gal1 protein.

In still another particular embodiment of the invention, the nucleic acid sequence (i) encodes a polypeptide comprising or consisting in the sequence SEQ ID NO: 38.

```
SEQ ID NO: 38 MDYKDDDDKGLLVFVRNLLLALCLFLVLGFLYYSAWKL
              HLLQWEEDSSKYSHSSGSEASFQVWNKDSSSKNLIPRL
              QKIWKNYLSMNKYKVSYKGPGPGIKFSAEALRCHLRDH
              VNVSMVEVTDFPFNTSEWEGYLPKESIRTKAGPWGRCA
              VVSSAGSLKSSQLGREIDDHDAVLRFNGAPTANFQQDV
              GTKTTIRLMNSQLVTTEKRFLKDSLYNEGILIVWDPSV
              YHSDIPKWYQNPDYNFFNNYKTYRKLHPNQPFYILKPQ
              MPWELWDILQEISPEEIQPNPPSSGMLGIIIMMTLCDQ
              VDIYEFLPSKRKTDVCYYYQKFFDSACTMGAYHPLLYE
              KNLVKHLNQGTDEDIYLLGKATLPGFRTIHC
```

This sequence SEQ ID NO: 38 consists in an amino acid sequence corresponding to a chimeric peptide comprising the anchor sequence of the human ST3Gal3 protein fused to the catalytic domain of the human ST6Gal1 protein.

In still another particular embodiment of the invention, the nucleic acid sequence (i) encodes a polypeptide comprising or consisting in the sequence SEQ ID NO: 39.

SEQ ID NO: 39 MDYKDDDDKGLLVFVRSWMLAALTLLVVFLIFAKEPQT
KPSRHQRTENIKERSLQSLAKPKSQAPTRARRTTGSEA
SFQVWNKDSSSKNLIPRLQKIWKNYLSMNKYKVSYKGP
GPGIKFSAEALRCHLRDHVNVSMVEVTDFPFNTSEWEG
YLPKESIRTKAGPWGRCAVVSSAGSLKSSQLGREIDDH
DAVLRFNGAPTANFQQDVGTKTTIRLMNSQLVTTEKRF
LKDSLYNEGILIVWDPSVYHSDIPKWYQNPDYNFFNNY
KTYRKLHPNQPFYILKPQMPWELWDILQEISPEEIQPN
PPSSGMLGIIIMMTLCDQVDIYEFLPSKRKTDVCYYYQ
KFFDSACTMGAYHPLLYEKNLVKHLNQGTDEDIYLLGK
ATLPGFRTIHC

This sequence SEQ ID NO: 39 consists in an amino acid sequence corresponding to a chimeric peptide comprising the cytoplasmic domain of human ST3Gal3, the transmembrane domain of human ST8Sia2, and the stem region of human ST8Sia2 fused to the catalytic domain of the human ST6Gal1 protein.

According to the invention, the transformed mammalian cell comprises at least one nucleic acid sequence (ii) encoding a therapeutic protein.

According to the present invention, such a therapeutic protein may be an enzyme, a hormone, an antibody or any protein which could have a medical interest.

Examples of therapeutic proteins that can be comprised in said nucleic acid sequence (ii) of the invention thus include, but are not limited to, erythropoietin (EPO), clotting factors such as Factor VII, Factor IX, Factor X, Protein C, antithrombin III or thrombin, carbohydrate antigens and serum biomarkers, cytokines such as interferon α, interferon β, interferon γ, interferon ω, Granulocyte-colony Stimulating Factor (GCSF) or Granulocyte Macrophage Colony-Stimulating Factor (GM-CSF), receptors, antibodies or immunoglobulins such as IgG, IgG fragments, IgG fusions, and IgM, soluble IgE receptor α-chain, immuno-adhesion proteins and other Fc fusion proteins such as soluble TNF receptor-Fc fusion proteins; RAGE-Fc fusion protein, interleukins; urokinase; chymase; and urea trypsin inhibitor; IGF-binding protein; growth factors such as epidermal growth factor (EGF) or vascular endothelial growth factor (VEGF); annexin V fusion protein; angiostatin, myeloid progenitor inhibitory factor-1; osteoprotegerin, α-1-antitrypsin; α-fetoproteins, DNaseII, human plasminogen, Kringle 3 domain of human plasminogen; glucocerebrosidase; TNF binding protein 1; Follicle stimulating hormone; Thyroid-stimulating hormone, Chorionogonadotropin, Luteinizing Hormone, cytotoxic T lymphocyte associated antigen 4-Ig; transmembrane activator and calcium modulator and cyclophilin ligand; glucagon like protein 1, IL-15 or IL-2 receptor agonist.

In a preferred embodiment, the transformed mammalian cell of the invention comprises at least one nucleic acid sequence (ii) encoding a glycoprotein hormone such as FSH, LH, TSH, and hCG.

In another preferred embodiment, the transformed mammalian cell of the invention comprises at least one nucleic acid sequence (ii) encoding an antibody or a fragment thereof, preferably a therapeutic antibody or a fragment thereof.

An antibody is an immunoglobulin molecule corresponding to a tetramer comprising four polypeptide chains, two identical heavy (H) chains (about 50-70 kDa when full length) and two identical light (L) chains (about 25 kDa when full length) inter-connected by disulfide bonds. Light chains are classified as kappa and lambda. Heavy chains are classified as gamma, mu, alpha, delta, or epsilon, and define the antibody's isotype as IgQ IgM, IgA, IgD, and IgE, respectively. Each heavy chain is comprised of an N-term heavy chain variable region (abbreviated herein as HCVR) and a heavy chain constant region. The heavy chain constant region is comprised of three domains (CH1, CH2, and CH3) for IgQ IgD, and IgA; and four domains (CH1, CH2, CH3, and CH4) for IgM and IgE. Each light chain is comprised of an N-term light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well-known conventions (KABAT, "Sequences of Proteins of Immunological Interest", National Institutes of Health, Bethesda, Md., 1987 and 1991; Chothia and Lesk (1987) Canonical structures for the hypervariable regions of immunoglobulins, J. Mol. Biol., 196: 901-17; Chothia et al. (1989). Conformations of immunoglobulin hypervariable regions, Nature, 342: 878-83). The functional ability of the antibody to bind a particular antigen depends on the variable regions of each light/heavy chain pair, and is largely determined by the CDRs.

Preferably, the antibody of the invention is an IgG immunoglobulin, more preferably an IgG1, an IgG2 or IgG4.

The term "antibody", as used herein, refers to a monoclonal antibody per se. A monoclonal antibody can be a human antibody, chimeric antibody, humanized and/or fully human antibody.

The invention also encompasses functional fragments of an antibody.

The term "functional fragments" as used herein refers to antibody fragment capable of reacting with its reaction target, such as for example, but not limited to, antigens comprising surface or tumoral antigens, receptors, etc. Such fragments can be simply identified by the skilled person and comprise, as an example, diabodies, monobodies, nanobodies, Fab fragment (e.g., by papain digestion), Fab' fragment (e.g., by pepsin digestion and partial reduction), F(ab')2 fragment (e.g., by pepsin digestion), Facb (e.g., by plasmin digestion), Fd (e.g., by pepsin digestion, partial reduction and reaggregation), and also scFv (single chain Fv; e.g., by molecular biology techniques) fragment are encompassed by the invention.

Depending on their nature, such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')2 heavy chain portion can be designed to include DNA sequences encoding the CH1 domain and/or hinge region of the heavy chain. The various portions of antibodies can be joined together chemically by conventional techniques, or can be prepared as a contiguous protein using genetic engineering techniques.

The term "Fc fragment" refers to a fragment of an antibody, said fragment being the support of biological properties of the immunoglobulin, and particularly its capacity to be recognized by the effectors of immunity, the complement or lectin receptors. The Fc fragment is constituted by constant fragments of heavy chains CH2 and CH3.

Preferably, the Fc fragment is derived form an IgG1 antibody.

The term "therapeutic" referring to an antibody, a functional fragment or derivative thereof designates more specifically any antibody, functional fragment or derivative thereof that functions to deplete target cells or molecules in a patient. Specific examples of such target cells include tumor cells, virus-infected cells, allogenic cells, pathological immunocompetent cells {e.g., B lymphocytes, T lymphocytes, antigen-presenting cells, etc.) involved in cancers, allergies, autoimmune diseases, allogenic reactions. Most preferred target cells within the context of this invention are immune cells, tumor cells and virus-infected cells. The therapeutic antibodies may, for instance, mediate B-lymphocyte depletion (anti-inflammatory antibodies such as anti-CD20 antibodies) or a cytotoxic effect or cell lysis (pro-inflammatory antibodies), particularly by antibody-dependent cell-mediated cytotoxicity (ADCC). Therapeutic antibodies according to the invention may be directed to circulatory mediators of inflammation, cell surface epitopes overexpressed by cancer cells, or viral epitopes.

In a preferred embodiment, a therapeutic antibody according to the invention is a human antibody.

In another preferred embodiment, a therapeutic antibody is a chimeric antibody.

By "chimeric antibody" is meant an antibody that is composed of variables regions from a non-human (particularly a murine) immunoglobulin and of constant regions of a human immunoglobulin. This alteration consists simply of adding the variable regions of a murine antibody to the human constant region, thus resulting in a human/non-human (particularly a human/murine) chimera which may be acceptable for pharmaceutical use.

A number of methods for producing such chimeric antibodies have been reported, thus forming part of the general knowledge of the skilled artisan (See, e.g., U.S. Pat. No. 5,225,539).

In another preferred embodiment, a therapeutic antibody is a humanized antibody.

By "humanized antibody" is meant an antibody that is composed partially or fully of amino acid sequences derived from a human antibody germline by altering the sequence of an antibody having non-human complementarity determining regions (CDR). This humanization of the variable region of the antibody and eventually the CDR is made by techniques that are by now well known in the art.

As an example, British Patent Application GB 2188638A and U.S. Pat. No. 5,585,089 disclose processes wherein recombinant antibodies are produced where the only portion of the antibody that is substituted is the complementarity determining region, or "CDR". The CDR grafting technique has been used to generate antibodies which consist of murine CDRs, and human variable region framework and constant regions (See. e. g., RIECHMANN et al., Nature, vol. 332, p: 323-327, 1988). These antibodies retain the human constant regions that are necessary for Fc dependent effector function, but are much less likely to evoke an immune response against the antibody.

Preferably, a humanized antibody again refers to an antibody comprising a human framework, at least one CDR from a non-human antibody, and in which any constant region present is substantially identical to a human immunoglobulin constant region, i.e., at least about 85 or 90%, preferably at least 95% identical. Hence, all parts of a humanized antibody, except possibly the CDRs, are substantially identical to corresponding parts of one or more native human immunoglobulin sequences. For example, a humanized immunoglobulin would typically not encompass a chimeric mouse variable region/human constant region antibody.

Most preferably, the constant regions from human light and heavy chains of the antibody of the invention are selected in a group comprising light and heavy chain constant regions corresponding to IgG1.

Examples of constant regions from human light and heavy chains are well known in the art. An example of human gamma 1 constant region is described in SHITARA et al (*Cancer Immunol. Immunother.*, vol. 36, p: 373-380, 1993).

In another preferred embodiment, a therapeutic antibody is selected among the group comprising rituximab, trastuzumab, cetuximab, motavizumab, palivizumab, alemtuzumab, but also comprising for instance, abciximab, adalimumab, alemtuzumab, basiliximab, belimumab, benralizumab, bevacizumab, brentuximab, canakinumab, catumaxomab, daratumumab, elotuzumab, epratuzumab, farletuzumab, galiximab, gemtuzumabozogamicin, golimumab, ibritumomabtiuxetan, ipilimumab, lumiliximab, necitumumab, nimotuzumab, ocrelizumab, ofatumumab, omalizumab, oregovomab, pertuzumab, raxibacumab, tocilizumab, tositumomab, ustekinumab, zalutumumab, and zanolimumab, preferably infliximab.

Sequences of these antibodies are well known in the art and can be simply identified by the skilled person Nucleic acid sequences (i) and (ii) comprised in said transformed mammalian cell may be comprised in one or more vectors present in said cell or in the genome of said cell.

The term "vector" (or "cloning vector" and "expression vector") means the vehicle by which a nucleic acid sequence can be introduced into a host cell, so as to transform the host and promote expression (e.g. transcription and translation) of the transfected sequence.

Typically, a nucleic acid sequence of the invention may be included in any suitable vector, such as a plasmid, cosmid, episome, artificial chromosome, phage or a viral vector.

Such vectors comprise necessary elements well known by one skilled in the art, such as an ori site. Such vectors may comprise regulatory elements, such as a promoter, enhancer, terminator, polyadenylation region and the like, to cause or direct expression of said polypeptide upon administration to a subject. Examples of promoters and enhancers used in the expression vector for animal cell are well known in the art and include early promoter and enhancer of SV40, LTR promoter and enhancer of Moloney mouse leukemia virus (Mo-MuLV), promoter and enhancer of immunoglobulin H chain and the like. Such vectors may also comprise resistance gene(s) for an easier selection.

According to the invention, any expression vector for animal cell can be used, so long as a nucleic acid sequence of the invention can be inserted and expressed. Examples of suitable vectors include pAGE107, pAGE103, pHSG274, pKCR, pSG1 beta d2-4, pIRES and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO94/19478.

According to the invention, each nucleic acid sequences (i) and (ii) is operatively linked to a promoter.

As used herein, the expression "Operably linked to a promoter" refers to a linkage in which the promoter is contiguous with the nucleic acid of interest to control the expression of said nucleic acid.

Examples of promoters that can be used in the transformed mammalian cells of the invention comprise, but are not limited to EPO promoter, GH promoter, CMV promoter, hEF 1-HTLV, SV40 promoter, Mo-MuLV LTR promoter.

According to the invention, the transformed mammalian cell is able to express the therapeutic protein encoded by the nucleic acid sequence (ii) as described above, with a sialylation on its at least one glycosylation site.

As used herein, the term "glycosylation site" refers to a N- and/or O-glycosylation site.

As used herein the term "sialylation" refers to N- or O-glycans containing 6-linked sialic acid.

The term "6-linked sialic acid" refers to the glycosidic bond between the position 2 of a sialic acid residue to the position 6 of an adjacent galactose residue.

Particularly, the transformed mammalian cell expresses the therapeutic protein with a sialylation on at least 2% of its glycosylation site(s), preferably at least 5% of its glycosylation site(s), and most preferably at least 7.5% of its glycosylation site(s).

In one embodiment of the invention, the transformed mammalian cell expresses the therapeutic protein with a digalactosylation on at least 10% of the N-glycosylation site(s) of said therapeutic protein.

As used herein, the term "digalactosylation" refers to a N-glycosylation site, wherein two galactose residues are linked to the underlying N-acetylglucosamine residues.

In another preferred embodiment of the invention, at least 70% of the sialylated glycans of the therapeutic protein are of the bi-, tri- and/or tetra-antennary type.

Sialylated glycan of bi-antennary type correspond to a N-linked glycan with two antennae of the N-acetyllactosaminic type terminated in 3/6 linked sialic acid.

Sialylated glycan of tri-antennary type correspond to a N-linked glycan with three antennae of the N-acetyllactosaminic type terminated in 3/6 linked sialic acid.

Sialylated glycan of tetra-antennary type correspond to a N-linked glycan with four antennae of the N-acetyllactosaminic type terminated in 3/6 linked sialic acid.

A second aspect of the invention relates to a method for producing a therapeutic protein with sialylation on the at least one glycosylation site of said protein, wherein said method comprises the steps of:
  a) culturing a transformed mammalian cell as described above;
  b) purifying the therapeutic protein encoded by nucleic acid sequence(s) (ii).

In a particular embodiment, the heterologous nucleic acid sequence (i) encodes
  a polypeptide consisting in SEQ ID NO: 1, SEQ ID NO: 43, or a derivative thereof, or
  a secreted polypeptide comprising SEQ ID NO: 1, SEQ ID NO: 43, or a derivative thereof.

In one embodiment, the step (b) of purifying the therapeutic protein encoded by the nucleic acid sequence (ii) is performed by harvesting the culture medium from the culture of step (a).

In one embodiment, the first nucleic acid sequence (i) and the second nucleic acid sequence (ii) are expressed in two distinct mammalian cells, the step a) of the method of the invention thus corresponding to the following steps:
  a1) culturing the transformed mammalian cell expressing the first nucleic acid sequence (i) and purifying the corresponding polypeptide;
  a2) culturing the transformed mammalian cell expressing the first nucleic acid sequence i) and purifying the corresponding polypeptide; and
  a3) contacting both polypeptides in conditions allowing sialylation by the polypeptide encoded by the first nucleic acid sequence (i) of the polypeptide expressed by the second nucleic acid sequence (ii).

In another embodiment of the invention, the method of the invention comprises a former step a') of transforming a mammalian cell with
  a first nucleic acid sequence (i) operatively linked to a promoter, wherein said nucleic acid sequence (i) encodes a polypeptide comprising the catalytic domain of ST6GAL1 defined by the sequence SEQ ID NO: 1, the catalytic domain of ST6GAL2 defined by the sequence SEQ ID NO: 43, or a derivative thereof and, and/or
  a second nucleic acid sequence (ii) operatively linked to a promoter, wherein said nucleic acid sequence (ii) encodes a therapeutic protein.

According to the invention, mammalian cells that can be used for this former step are from the same type to the transformed mammalian cells of the invention. Preferably, said mammalian cells are CHO cells, HEK-293 cells, COS cells, NSO cells, PER.C6® or SP2O cells.

In another embodiment of the invention, the step b) also comprise the determination of the glycosylation pattern of the therapeutic protein.

Methods for determining the glycosylation pattern are well known in the art.

Preliminary information about glycosylation in general and sialylation of the therapeutic protein can be obtained by affino-binding and/or immunoblotting analysis using specific probes such as lectins (CON A; LCA, GNL, ECL, SNA, PSL, MAA, WGA . . . ) and/or specific N-glycans antibodies (anti-1,2-xylose; anti-1,3-fucose; anti-Neu5Gc, anti-Lewis . . . ). To investigate the detailed N-glycan profile of recombinant polypeptide, N-linked oligosaccharides is released from the polypeptide in a non specific manner using enzymatic digestion or chemical treatment. The resulting mixture of reducing oligosaccharides can be profiled by HPLC and/or mass spectrometry approaches (ESI-MS-MS and MALDI-TOF essentially). These strategies, coupled to exoglycosidase digestion, enable N-glycan identification and quantification (SEVENO et al., *Anal. Biochem.*, vol. 379, p: 66-72, 2008; STADLMANN et al., *Proteomics*, vol. 8, p: 2858-2871, 2008).

Another alternative to study glycosylation pattern of a recombinant protein (for example therapeutic protein of the invention) is to work directly on the glycopeptides obtained after its digestion by protease, by their purification and their analysis by mass spectrometry as disclosed in BARDOR et al. (*Plant Biotechnol. J.*, vol. 1, p: 451-462, 2003).

In a particular embodiment, said step of determining the glycosylation pattern of said produced therapeutic protein is done by determining the sialylation of said therapeutic protein.

Still preferably, the method of the invention comprises the step b) of determining the glycosylation pattern of the therapeutic protein obtained in step a) and purifying the therapeutic protein with i) a sialylation on at least 2% of its glycosylation site(s), preferably at least 5% of its glycosylation site(s), and most preferably at least 7.5% of its glycosylation site(s) or eventually 10% of its glycosylation site(s), or even 15% or 20% of its glycosylation site(s).

In fact, the method of the invention enables the obtaining of recombinant antibodies (or fragments thereof, Fc) having a glycoprotein profile similar to the one in human sera (See tables II and IV); these recombinant antibodies or fragments being obtained in large amounts from mammalian cells transformed with the polypeptides described previously.

In a preferred embodiment, the therapeutic protein is selected among antibodies and fragments thereof, preferably therapeutic antibodies and fragments thereof.

Preferably, the method of the invention comprises the step b) of determining the glycosylation pattern of the therapeutic protein obtained in step a) and purifying the antibody or fragment thereof with i) a G2FS2 glycosylation profile on more than 1% of the produced glycosylated antibody or fragment thereof.

Moreover, the inventors established surprisingly that unlike the strict α-1,3 branch specificity sialylation of wild type ST6Gal-I for glycoproteins (BARB et al., *Biochemistry*, vol. 48(41), p: 9705-9707, 2009), the soluble catalytic domain of ST6Gal-I (SEQ ID NO: 1) has the capacity to glycosylate significantly other branches (e.g. Tables II and IV (See G2F2S) and Table III: glycoproteins having multi-branches profiles with more than 70% of glycosylation).

Thus and in another preferred embodiment, the therapeutic protein is selected among (ii) encoding a glycoprotein hormone such as FSH, LH, TSH, and hCG.

In this preferred embodiment, the method of the invention enables to purify the therapeutic protein with i) a sialylation on at least 50% of its glycosylation site(s), preferably at least 60% of its glycosylation site(s), and most preferably at least 65% of its glycosylation site(s) or eventually 70% of its glycosylation site(s). Again still preferably, the step b) is realized on therapeutic protein with a digalactosylation on at least 10% of the N-glycosylation site(s) of said therapeutic protein.

More still preferably, the step b) is realized on therapeutic protein comprising at least 70% of the sialylated glycans of the bi-, tri- and/or tetra-antennary type.

A third object of the invention aims to provide the use of a transformed mammalian cell of the invention for producing a therapeutic protein comprising at least one glycosylation site with a sialylation on said at least one glycosylation site.

Preferably, said use is for producing a therapeutic protein with a sialylation on at least 2% of its glycosylation site(s), preferably at least 5%, more preferably at least 7.5% or eventually at least 10% of its glycosylation site(s), or even 15% or 20% of its glycosylation site(s).

In a preferred embodiment, the therapeutic protein is selected among antibodies and fragments thereof, preferably therapeutic antibodies and fragments thereof. In another preferred embodiment, the therapeutic protein is selected among (ii) encoding a glycoprotein hormone such as FSH, LH, TSH, and hCG. In said preferred embodiment, said use is for producing a therapeutic protein with a sialylation on at least 50% of its glycosylation site(s), preferably at least 60% of its glycosylation site(s), and most preferably at least 65% of its glycosylation site(s) or eventually 70% of its glycosylation site(s).

Still preferably, said use is also for producing a therapeutic protein with a digalactosylation on at least 10% of the N-glycosylation site(s) of said therapeutic protein.

Again still preferably, said use is also for producing a therapeutic protein, wherein at least 70% of the sialylated glycans are of the bi-, tri- and/or tetra-antennary type.

A fourth object of the invention concerns a therapeutic protein which can be obtained by the method of the invention.

In one preferred embodiment, said therapeutic protein is an antibody or fragment thereof, preferably a Fc fragment.

According to the invention, said therapeutic protein has a sialylation on at least 2% of its glycosylation site(s), preferably at least 5% of its glycosylation site(s), and most preferably at least 7.5% or eventually 10% of its glycosylation site(s).

According to the invention, said therapeutic protein has a digalactosylation on at least 10% of its N-glycosylation site(s).

Finally, at least 70% of the sialylated glycans of said therapeutic protein are of the bi-, tri- and/or tetra-antennary type.

A fifth object of the invention concerns a pharmaceutical composition comprising a therapeutic protein which can be obtained or directly obtained by the method of the invention.

Said composition may be in any pharmaceutical form suitable for administration to a patient, including but not limited to solutions, suspensions, lyophilized powders, capsule and tablets.

In a preferred embodiment, said pharmaceutical composition may further comprise a pharmaceutically acceptable carrier selected among pharmaceutically acceptable diluent, excipient or auxiliary.

The pharmaceutical composition of the invention may be formulated for injection, e.g. local injection, mucosal administration, inhalation, oral administration and more generally any formulation that the skilled person finds appropriate to achieve the desired prognosis and/or diagnosis and/or therapy.

The therapeutic protein is contained in said pharmaceutical composition in an amount effective for achieving the intended purpose, and in dosages suitable for the chosen route of administration.

More specifically, a therapeutically effective dose means an amount of a compound effective to prevent, alleviate or ameliorate symptoms of the disease or condition of the subject being treated, or to arrest said disease or condition.

Depending on the intended application, the therapeutic protein according to the invention may further comprise additional constituents.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

Example 1

Material and Methods
Cell Culture.
CHO K1 or CHO CCL61 wild-type (ATCC) cell lines of the invention were used to produce the Fc domain of IgG1 antibody. Cell cultures were performed in Ham's F12 Medium with L-glutamine supplemented with fetal bovine serum (FBS) deprived or not in immunoglobulins in the presence antibiotics (G418 for cells containing one Sialyltransferase, zeocin for cells containing the Fc gene, both antibiotics for cells doubly transfected) with or without penicillin and streptomycin. Cells were grown in incubator at 37° C. at optimal humidity and oxygen content as recommended.

Cell Transfection

Plasmids

All Sialyltransferase constructions (nucleic acid sequence (i) of the invention) were encoded into pcDNA3.1(+) vector (INVITROGEN), containing an ampicillin resistance gene for selection in bacteria and a geneticin(G418) resistance gene for selection in mammalian cells.

As a nucleic acid sequence (ii) of the invention, Fc gene was encoded into pFUSE vector (INVIVOGEN) containing a zeocin resistance gene.

Transient Transfection

Cells were coated the day before in 24-wells plates and cultured in medium Ham's F12 containing FBS without antibiotic. Prior transfection, condition media was changed to chemically defined medium free of FBS and antibiotics. Expression vector containing either a sialyltransferase minigene and/or the Fc minigene was transferred in CHO cells using a transfection reagent (FUGENE6, ROCHE, FREESTYLE, INVITROGEN, TRANSITPRO, EUROMEDEX) according to manufacturer's instruction. For double transfection (ST+Fc) cells were transfected at a preferred ratio ST/Fc of 3:1, ratio transfection agent/DNA was kept at the same ratio used for single transfection. After 3 days post transfection, condition media was collected for analysis.

Stable Clone Generation

CHO cells are initially seeded in a 6-well plate in presence of Ham's F12 medium+5% FBS and incubate for 24 hours at 37° C. Cells are washed before addition of chemically defined medium. CHO cells are then transfected with pcDNA3.1 plasmids containing sialyltransferase or Fc encoding genes using the transfectant reagent (FUGENE6, ROCHE) at various ratios (3:2, 3:8 and 4:5 (µL/µg)) and incubate overnight. Media are removed and wells washed once with DPBS. After addition of new medium containing FBS, cells were incubated for 24 hours after transfection. For cell recovery, condition medium is then replaced with fresh medium/FBS antibiotic free medium.

To select cells that have stably incorporated the plasmid into their genomic DNA, the medium is removed and replaced with fresh medium containing FBS, G418 and/or zeocin. Cells are then split repeatedly for about 3 weeks in new selective medium containing FBS and G418. G418 concentration was progressively increased to select fully resistant cells.

Resistant cells were harvested and cloned by limited dilution. Stable clones were propagated in selection medium. Every single clone was transferred from 96-well to 24-wells plates. Each selected clone was propagated at a reduced amount of G418 for maintenance and aliquots were frozen at −80° C.

Immunostaining

After overnight incubation, cloned cells attached to the coverglass are rinsed with DPBS containing $Ca^{++}$ and $Mg^{++}$ three times. Each coverglass is fixed with PBS/PFA 4% and washed before PBS/BSA 1% is added for saturation. Staining solution with SNA-FITC I performed in DPBS with $Ca^{++}$ and $Mg^{++}$. After incubation, stained coverglass are washed and microslides are dry-cleaned. Prolong gold-DAPI reagent is deposited on the microslide along with one drop of prolong gold on cells. Positive stained cells are counted with regard to the total number of cells based on nuclear staining.

Small and Medium Scale Protein Production.

Genetically engineered CHO cells expressing a polypeptide comprising the catalytic domain of ST6Gal1 human sialyltransferase and the Fc domain of antibody IgG1 are seeded into T-175 flasks (FALCON) or 5 layer stacks (FALCON) in the presence of FBS. Cells are then washed and placed into a serum free medium. The supernatant was collected at various times and filtered.

Protein A Purification.

Column Preparation

Fc purification from condition medium was performed by affinity chromatography using protein A-agarose resin (SIGMA). Columns were prepared by pouring protein A-agarose resin into a disposable column (GEHEALTHCARE). The packed affinity resin was then repeatedly washed with washing/binding buffer (0.02 M $NaH_2PO_4$, 0.15 M NaCl, pH 8).

Sample Purification

Samples were applied to the column by layering onto the top of the resin. Column was repeatedly washed with the washing/binding buffer. before it is Fc eluted by adding the elution buffer (01 M Glycine, pH 3). Eluates are neutralized by a TRIS buffer pH 9.

Sample concentration is then performed using the AMICON Ultra centrifugal filters (MILLIPORE). The protein is concentrated by spinning at 3000 g, 4° C. down to a volume below 250 µl.

Sna Purification.

Purification columns were prepared by packing SNA-agarose (CLINISCIENCES) into the column. Before loading Fc containing sample onto the column, the resin was washed with a PBS washing buffer containing 0.1 mM $CaCl_2$). After binding, columns are washed and elution performed with the elution buffer (25 mM PBS, 0.1 mM $CaCl_2$, 0.5 M lactose).

Fc Assay

Fc Dosing in Cell Medium

Fc produced in cell medium is assayed by ELISA (enzyme-linked immunosorbent assays). Protein A (SIGMA, P7837) is coated in 96-wells plates (IMMULON UHB) for 2 h at room temperature. After washing with PBS, saturation is achieved with BSA in PBS. After overnight incubation and washing, biotinylated antibody (INVITROGEN) is added to the wells and allowed to bind for 2 hrs. After washing, before streptavidin-HRP is added (SIGMA were added. Detection was performed by adding citrate phosphate buffer pH 4.2 (SIGMA) in the presence of ABTS 0.5 mg/mL (SIGMA) and 0.03% $H_2O_2$. Optical density is measured at 405 nm.

Fc Dosing in Serum

Fc in mouse plasma is assayed by ELISA based on coating streptavidin in PBS 50 mM pH 7.4 in 96-wells plate. Saturation is performed with BSA. Samples are allowed to bind overnight at 4° C. or 2 h at room temperature. After washing, a biotinylated antibody INVITROGEN is added in each well for 2 hrs followed by a polyclonal anti-Fc-HRP. Detection was performed by adding citrate phosphate buffer pH 4.2 (SIGMA) in the presence of ABTS (SIGMA) and $H_2O_2$. Optical density of each is measured at at 405 nm.

Extraction of Engineered Cells Protein.

After medium scale production, cells were collected and rinsed with PBS. Cells were centrifuged. Pellets were dried and resuspended in 100% ethanol. The mixture was incubated for 24 h at −20° C. followed by another centrifugation step. The ethanol layer was discarded. Pellets were resuspended in 50 mM Phosphate buffer pH7.3. Cells were lysed with repeated freezing/thawing cycles in ethanol/dry ice followed with sonication. Each extract is denatured in SDS and b-mercaptoethanol, and deglycosylated with PNGase F (ROCHE 11 365 193 001) at 37° C. for 15 hrs. Free N-glycans are purified on carbograph (ALLTECH) and permethylated with DMSO, NaOH, ICH3 before desalting on Sep Pack C18 (WATERS). They are then lyophilized and concentrated on ZIPTIP C18 (MILLIPORE). Elution was performed with 80% acetonitrile. After another lyophilization, N-glycans were resuspended in methanol/$H_2O$ 50:50.

ELLA (Enzyme Linked Lectin Assay).

Analysis of Fc sialylation is performed by Enzyme-linked-lectin assay (ELLA). ELISA specific plates were coated with streptavidin in 50 mM PBS pH 7.4 and incubated overnight at 4° C. After washing with PBS 50 mM pH 7.4, TWEEN 0.05% wells are saturated with BSA. The plates were then washed and incubated with biotinylated lectin (VECTOR lab.) as recommended by the manufacturer. Fc samples are allowed to bind for 2 h at room temperature. Captured Fcs are detected by a goat anti-Fc antibody in F12 5% SVF followed by a polyclonal rabbit anti-goat HRP antibody. Each antibody addition was followed by a 1 h incubation period at 37° C. and 5 washes. Detection is performed by adding citrate phosphate buffer pH 4.2 (SIGMA) in the presence of ABTS (SIGMA and H2O2. Optical density is measured at 405 nm.

Gel Electrophoresis.

Proteins were diluted in 4× NuPAGEZ LDS sample buffer and 10×NuPAGE reducing agent. Volumes were adjusted with $H_2O$ before 10 min heating at 70° C. Loading is achieved on precast NuPAGENovexBis-Tris Mini gel. Gels are run at 200V for 1 hr in MOPS buffer. Gels are stained using Coomassie blue.

Mass Spectrometry.

Protein are denatured in SDS and b-mercaptoethanol and deglycosylated with PGNase F (ROCHE). Free glycans are purified and permethylated in DMSO, NaOH, ICH3 before desalting using Sep Pack C18 column (WATERS). After lyophilization, N-glycans were resuspended in methanol/$H_2O$ and analyzed using MALDI TOF Mass spectrometer. Permethylated glycans are crystallized in DHM matrix in methanol. Spectra were acquired at positive mode with acceleration voltage set at 20 kV, grid voltage 75%, guide wire at 0.002% and delay tile at 175 ns.

Pharmacokinetic Studies.

After a week of acclimation, C15BL/6 mice receive a single IV injection of antibody at a dose 1-5 mg/kg of Fc. Blood samples are collected via retro-orbital bleeding at time intervals and 3 mice were bled at each time points. After addition of heparin, samples were centrifuged to obtain plasma. Samples were frozen until estimation by ELISA.

Results

The inventors thus produced antibody and Fc fragments using a transformed cell of the invention.

They studied the influence of the presence of the catalytic domain of the human ST6Gal1 sialyltransferase in said transformed cell on sialylation of produced antibody and Fc fragment.

As a control, they used a transformed cell expressing the Fc fragment (SEQ ID NO: 40) but which does not comprise a nucleic acid sequence encoding a polypeptide comprising the catalytic domain of ST6GAL1 human sialyltransferase.

Results are showed in the table I below. Concerning the control, the produced Fc fragment was not sialylated (percentage of sialylation=0%).

The first column illustrates which sialyltransferase construct has been used to be expressed in the newly transformed cell. The second column describes the total amount of produced Fc fragment by said transformed cell, the third column shows the amount of glycosylated Fc fragment and the fourth column shows the amount of sialylated Fc fragment. The last column finally synthetizes the results by showing the percentage of sialylation obtained for each construction.

TABLE I

| Nucleic acid sequence (i) | Total Fc (ng) | Glycosylated Fc (ng) | Sialylated Fc (ng) | sialylation % |
|---|---|---|---|---|
| SEQ ID NO: 1 | 412 | 102 | 36 | 9 |
| SEQ ID NO: 35 | 130 | 40 | 13 | 10 |
| SEQ ID NO: 36 | 118 | 45 | 15 | 13 |
| SEQ ID NO: 37 | 122 | 38 | 13 | 13 |

These results show that the constructions and cells of the invention permits to obtain for the first time a substantial and variable sialylation of the Fc fragment.

Co-transfecting a CHO cell with a nucleic acid encoding a Fc fragment (nucleic acid sequence (ii) of the invention) and a nucleic acid sequence (i) of the invention encoding a polypeptide comprising the catalytic domain of ST6GAL1 human sialyltransferase permitted to obtain sialylated Fc fragments.

The table II below permits to compare the sialylation of the Fc fragment produced by a transformed cell of the invention—i.e. Fc1 (SEQ ID NO: 1), Fc2 (SEQ ID NO: 38), Fc3 (SEQ ID NO: 39)—, the glycosylation and sialylation of several commercialized therapeutic antibodies—i.e., A to E-and the sialylation of IgG1 immunoglobulins isolated from human sera.

TABLE II

| | Glycosylation distribution (as a percentage of the glycosylated proteins) | | | | | | | |
|---|---|---|---|---|---|---|---|---|
| Glycosylation | Antibodies produced in CHO cells | | | | | Fc fragment produced in cells of the invention | | |
| profile | A | B | C | D | E | Fc1 | Fc2 | Fc3 |
| G0F | 56.5 | 55.0 | 83.9 | 50.7 | 69.0 | 26.2 | 31.6 | 30.7 |
| G1F | 37.7 | 39.7 | 15.2 | 42.0 | 28.7 | 51.0 | 49.5 | 50.0 |
| G2F | 5.8 | 5.3 | 0.9 | 7.3 | 2.3 | 12.4 | 10.8 | 13.3 |
| G1FS1 (2,6NeuAc) | 0 | 0 | 0 | 0 | 0 | 1.9 | 1.1 | 0.5 |

TABLE II-continued

| | Glycosylation distribution (as a percentage of the glycosylated proteins) | | | | | | | |
|---|---|---|---|---|---|---|---|---|
| Glycosylation profile | Antibodies produced in CHO cells | | | | | Fc fragment produced in cells of the invention | | |
| | A | B | C | D | E | Fc1 | Fc2 | Fc3 |
| G2FS1 (2,6NeuAc) | 0 | 0 | 0 | 0 | 0 | 3.4 | 1.7 | 1.0 |
| G2FS2 (2,6NeuAc) | 0 | 0 | 0 | 0 | 0 | 1.1 | 0.2 | 0.2 |

Data concerning the commercialized antibodies (which are anonymous) produced in CHO, NSO or Sp2O cells can be found in WACKER et al. (*European Journal of Pharmaceutics and Biopharmaceutics*, 79 (2011) 503-507).

The sialylation corresponds to the three following glycans: G1FS1, G2FS1, and G2FS2. It is clear that the commercialized antibodies are not sialylated, independently of the expression system. In contrast, the cells of the invention permit to obtain both glycosylation (G0F+G1F+G2F) and sialylation (G1FS1+G2FS1+G2FS2) patterns close to the glycosylation and sialylation pattern of a circulating antibody. More especially, the sialylation pattern obtained with the only catalytic domain of human ST6Gal1 is the closest to the one of circulating IgG1.

Preliminary data identified that Fc produced in cells expressing SEQ ID NO: 1 displayed a long lasting component when injected in mice. It was determined an elimination phase with a $T^{1/2}$ (1)=7.12 hr, and a second much longer phase with a $T^{1/2}$ (2)=177.73 hr. This last fraction is far above what has been already described for other drug protein-Fc for which duration in blood never exceed 8 hr.

Overall, example 1 shows that producing therapeutic antibodies using cells of the invention delivers products with a prolonged half-life of the therapeutic antibody or Fc fusion protein, an improved effect and a decreased immunogenicity. This is a promising approach for an improved efficiency of protein drugs used in immunotherapy (IgG), Example 2

Similar studies have been carried out with a transformed cell of the invention comprising a nucleic acid sequence (ii) encoding the TSH hormone, the pregnancy hormone (hCG), a typical IgG1 or the Fc fragment.

Briefly, CHO cells have been transiently with the panel of constructions (nucleic acid sequence (i) of the invention) for 48-72 h. The content in sialylated forms was estimated using affinity chromatography or lectin binding (*, data below) and similar data were obtained. Accordingly, the data have been summarized in the single table III as shown below.

TABLE III

| | Sialylation of the protein of interest depending on the used CHO cell lines (nucleic acid sequence (i)) | | |
|---|---|---|---|
| Nucleic acid sequence (ii) | SEQ ID NO: 1 Delta 89 | SEQ ID NO: 35 CHO/ST6 | SEQ ID NO: 38 |
| TSH* | 72% | 74% | 68% |
| hCG* | 83% | 82% | 78% |
| hCGbeta | 85% | ND | 70% |
| IgG1/ (infliximab) | 18% | 16% | ND |
| Fc | 8% | 6% | 4% |

ND: not determined

In addition, no significant difference was found in the extent of sialylation among the transient and stable transfection: all the proteins produced by transient transfections proved to display the same glycoprofile as the corresponding stable clone(s).

In another series of experiment, we have further analyzed the glycosylation pattern of hCG, the pregnancy hormone as a representative of the gonadotropin family (hCG, hLH and hFSH). The results have shown that the glycosylation pattern obtained for hCG was very similar to the one of placental hCG (data not shown), which hormone is naturally a good acceptor of sialic acid even though its glycoprofile is very different from that of TSH, which has naturally a quite low content in sialic acid. Again, the glycoprofile of hCG is maintained during clone isolation as well as hormone production.

Altogether, these data show that the cells lines transformed with specific sialyltransferase constructs allow to achieve full completion of various glycoproteins including antibodies and glycoprotein hormones—e.g. TSH or gonadotropins—for which sialylation and especially 6-linked sialic acid is not especially the preferred sugar. Sialylated glycoprotein hormones exhibit a glycosylation pattern similar for that known to be expressed under normal (placental hCG) or pathological conditions (TSH is highly sialylated in primary hypothyroidism).

Finally, example 2 demonstrates that glycoproteins such as hormones can be advantageously produced in the cells of the invention to obtain unprecedented sialylated products for which therapeutic indications, ovarian stimulation (gonadotropins) or thyroid cancer (TSH), have been delivered for $1^{st}$ generation molecules.

Example 3: Expression of the Commercialized Antibody INFLIXIMAB in a Transformed Mammalian Cell of the Invention Infliximab is a recombinant antibody of the IgG1 family that binds and neutralizes TNF alpha in blood. This antibody comprises a single N-glycosylation site at position Asn297. The market product is produced in Sp2O cells and marketed under the trade name of REMICADE™.

We have expressed the heavy and light chains coding for Infliximab (SEQ ID NO: 41 and 42 respectively) in a CHO cell line further expressing SEQ ID NO: 1. As a control, we also expressed a Fc fragment (SEQ ID NO: 40) in the wild type CHO cell line.

As a negative control, we also expressed infliximab and the Fc fragment in a non transformed CHO cell line.

The produced antibody and Fc fragment have been purified on protein A as commonly performed for most marketed antibodies or fragment thereof, and then characterized by mass spectrometry analysis following a digestion with trypsin.

As a control, we determined by the same way, the glycosylation pattern of REMICADE. The data are summarized in the Table below with Fc (Fc-Sial) and Infliximab (Inf-Sial) produced in CHO cell lines expressing SEQ ID NO: 1, Fc (Fc) and Infliximab (Inf) produced in CHO cell lines and commercialized infliximab (REMICADE) produced in NSO cell lines.

The results are summarized in the table IV below.

TABLE IV

| | Glycan repartition for the different products (percentage) | | | |
|---|---|---|---|---|
| Glycan type | Fc-Sial | Fc | Inf-Sial | Inf |
| G0F | 33 | 41 | 26 | 37 |
| G1F | 35 | 45 | 31 | 45 |
| G2F | 10 | 8 | 7 | 12 |
| G1FS1 | 7 | 3 | 7 | 2 |
| G2FS1 | 6 | 3 | 7 | 3 |
| G2FS2 | 9 | 0 | 22 | 0 |

The results show that all products comprise variable ratios of incomplete fucosylated glycans (G0F, G1F and G2F). Considering the expression of sialylated variants, none were detected for the commercialized Infliximab—i.e. REMICADE—, small percentages were detected for Fc fragment and infliximab produced in CHO—i.e. 3%—, whereas a high expression of sialylated variants G1FS1, G2FS1 and G2FS2 were detected for Fc fragment and infliximab produced in the cells of the invention (15 and 29% respectively).

It has been described in the prior art that the effector functions of an antibody are heavily dependent on the single N-linked glycan of the heavy chain, which resides just below the hinge region. This sialylated glycan is believed to maintain the two heavy chains of the Fc in a constrained conformation required decreasing interactions with one or several types of Fc receptors. Data, still under debate, also demonstrated that sialylated antibodies may further initiate an anti-inflammatory cascade through the human lectin receptor called DC-SIGN.

Nor REMICADE or infliximab produced in CHO cell lines actually bind to a recombinant HEK cell line expressing DC-SIGN but they bind to human dendritic cells.

Binding of Infliximab produced in CHO cells stably transfected with SEQ ID NO: 1 to human dendritic cells is dose dependent, insensitive to EDTA and is not inhibited by preincubation with an anti-DC SIGN antibody (data not shown). In contrast to infliximab, REMICADE (produced in Sp2O cells with a different glycoprofile and no sialic acid) binds to a different receptor which binding is sensitive to EDTA.

Since infliximab and REMICADE contain similar content in G0F, G1F and G2F, it is concluded that sialic acid by itself prevents binding of the anti-TNF antibody to the EDTA sensitive receptor, while it does not affect recognition by other receptors present on the same cells.

In conclusion, Example 3 demonstrates that a single anti-TNF antibody produced in rodent cells expressing or not with the sialyl transferase of the invention display both an altered glycoprofile and different binding activity. It is shown that in human antigen-presenting cells, sialylation of infliximab targets recognition to distinct receptors. According to the literature, such glycosylation-based recognition may prevent activation of these cells and ultimately reduce antibody immunogenicity. These results may in part explains why REMICADE is immunogenic in patients treated with the drug and suggests that a sialylated form of infliximab may be a new way to prevent inappropriate recognition by immune cells.

Example 4. Branch Specific Sialylation of ST6GalI Vs the Catalytic Domain of ST6GalI Transferrin, alpha-foetoprotein and alpha1 acid glycoprotein are multi antennae glycoproteins comprising biantennary, triantennary and tetraantinnary glycans respectively.

We have expressed these proteins in a CHO cell line further expressing SEQ ID NO: 1. As a control, we also expressed the wild type ST6GalI in a CHO cell line.

The produced proteins were characterized by mass spectrometry analysis following a digestion with trypsin.

The results are summarized in the table V below.

TABLE V

| Asialo Acceptors with | Polypeptides | $EC_{50}$ | % sialylation |
|---|---|---|---|
| Transferrin Bi-antennary glycans | ST6 GalI | 0.18 | 25% |
| | SEQ ID NO: 1 | 0.7 | 100% |
| Alpha-foetoprotein Tri-antennary glycans | ST6 GalI | 0.3 | 52% |
| | SEQ ID NO: 1 | 0.75 | 100% |
| Alpha acid glycoprotein Tetraantennary glycans | ST6 GalI | 0.2 | 18% |
| | SEQ ID NO: 1 | 0.85 | 100% |

The results confirms the previous results that, unlike the ST6Gal I protein, its catalytic domain SEQ ID NO: 1 is able to sialylate multi-antennary glycoproteins without branch specificity leading to a great increase of sialylation yields for these glycoproteins.

Moreover, the obtaining of such glycosylation profiles with only one enzyme expressed in a transformed mammalian cell enable to provide a simple and efficient system for the expression of glycoproteins with high yields.

SEQUENCE LISTING

<160> NUMBER OF SEQ ID NOS: 43

<210> SEQ ID NO 1
<211> LENGTH: 317
<212> TYPE: PRT
<213> ORGANISM: Artificial Sequence
<220> FEATURE:
<223> OTHER INFORMATION: Catalytic domain of ST6Gal1 Sialyl transfirase

```
<400> SEQUENCE: 1

Glu Ala Ser Phe Gln Val Trp Asn Lys Asp Ser Ser Lys Asn Leu
1               5                   10                  15

Ile Pro Arg Leu Gln Lys Ile Trp Lys Asn Tyr Leu Ser Met Asn Lys
                20                  25                  30

Tyr Lys Val Ser Tyr Lys Gly Pro Gly Pro Gly Ile Lys Phe Ser Ala
            35                  40                  45

Glu Ala Leu Arg Cys His Leu Arg Asp His Val Asn Val Ser Met Val
50                  55                  60

Glu Val Thr Asp Phe Pro Phe Asn Thr Ser Glu Trp Glu Gly Tyr Leu
65                  70                  75                  80

Pro Lys Glu Ser Ile Arg Thr Lys Ala Gly Pro Trp Gly Arg Cys Ala
                85                  90                  95

Val Val Ser Ser Ala Gly Ser Leu Lys Ser Ser Gln Leu Gly Arg Glu
            100                 105                 110

Ile Asp Asp His Asp Ala Val Leu Arg Phe Asn Gly Ala Pro Thr Ala
            115                 120                 125

Asn Phe Gln Gln Asp Val Gly Thr Lys Thr Thr Ile Arg Leu Met Asn
130                 135                 140

Ser Gln Leu Val Thr Thr Glu Lys Arg Phe Leu Lys Asp Ser Leu Tyr
145                 150                 155                 160

Asn Glu Gly Ile Leu Ile Val Trp Asp Pro Ser Val Tyr His Ser Asp
                165                 170                 175

Ile Pro Lys Trp Tyr Gln Asn Pro Asp Tyr Asn Phe Phe Asn Asn Tyr
            180                 185                 190

Lys Thr Tyr Arg Lys Leu His Pro Asn Gln Pro Phe Tyr Ile Leu Lys
            195                 200                 205

Pro Gln Met Pro Trp Glu Leu Trp Asp Ile Leu Gln Glu Ile Ser Pro
            210                 215                 220

Glu Glu Ile Gln Pro Asn Pro Pro Ser Ser Gly Met Leu Gly Ile Ile
225                 230                 235                 240

Ile Met Met Thr Leu Cys Asp Gln Val Asp Ile Tyr Glu Phe Leu Pro
                245                 250                 255

Ser Lys Arg Lys Thr Asp Val Cys Tyr Tyr Gln Lys Phe Phe Asp
            260                 265                 270

Ser Ala Cys Thr Met Gly Ala Tyr His Pro Leu Leu Tyr Glu Lys Asn
            275                 280                 285

Leu Val Lys His Leu Asn Gln Gly Thr Asp Glu Asp Ile Tyr Leu Leu
            290                 295                 300

Gly Lys Ala Thr Leu Pro Gly Phe Arg Thr Ile His Cys
305                 310                 315

<210> SEQ ID NO 2
<211> LENGTH: 24
<212> TYPE: PRT
<213> ORGANISM: Artificial Sequence
<220> FEATURE:
<223> OTHER INFORMATION: transmemebrane domain of human ST6GalI

<400> SEQUENCE: 2

Cys Cys Val Leu Val Phe Leu Leu Phe Ala Val Ile Cys Val Trp Lys
1               5                   10                  15

Glu Lys Lys Lys Gly Ser Tyr Tyr
            20
```

```
<210> SEQ ID NO 3
<211> LENGTH: 20
<212> TYPE: PRT
<213> ORGANISM: Artificial Sequence
<220> FEATURE:
<223> OTHER INFORMATION: transmemebrane domain of CHO ST6GalI

<400> SEQUENCE: 3

Tyr Phe Ile Leu Ala Phe Leu Leu Phe Ala Leu Ile Cys Val Trp Lys
1               5                   10                  15

Lys Gly Ser Tyr
            20

<210> SEQ ID NO 4
<211> LENGTH: 21
<212> TYPE: PRT
<213> ORGANISM: Artificial Sequence
<220> FEATURE:
<223> OTHER INFORMATION: transmembrane domain of mouse ST6GalI

<400> SEQUENCE: 4

Cys Phe Val Leu Val Phe Leu Leu Phe Ala Ile Ile Cys Val Trp Lys
1               5                   10                  15

Lys Gly Ser Asp Tyr
            20

<210> SEQ ID NO 5
<211> LENGTH: 21
<212> TYPE: PRT
<213> ORGANISM: Artificial Sequence
<220> FEATURE:
<223> OTHER INFORMATION: transmembrane domain of rat ST6GalI

<400> SEQUENCE: 5

Leu Phe Ile Leu Val Phe Leu Leu Phe Ala Val Ile Cys Val Trp Lys
1               5                   10                  15

Lys Gly Ser Asp Tyr
            20

<210> SEQ ID NO 6
<211> LENGTH: 21
<212> TYPE: PRT
<213> ORGANISM: Artificial Sequence
<220> FEATURE:
<223> OTHER INFORMATION: TMD human ST6GalII

<400> SEQUENCE: 6

Met Leu Phe Gly Ile Phe Ala Trp Gly Leu Leu Phe Leu Ile Phe
1               5                   10                  15

Ile Tyr Phe Thr Asp
            20

<210> SEQ ID NO 7
<211> LENGTH: 21
<212> TYPE: PRT
<213> ORGANISM: Artificial Sequence
<220> FEATURE:
<223> OTHER INFORMATION: transmembrane domain CHO ST6GalII

<400> SEQUENCE: 7

Met Leu Phe Gly Ile Phe Val Trp Gly Leu Leu Phe Leu Ala Ile Phe
1               5                   10                  15

Ile Tyr Phe Thr Asn
            20
```

```
<210> SEQ ID NO 8
<211> LENGTH: 21
<212> TYPE: PRT
<213> ORGANISM: Artificial Sequence
<220> FEATURE:
<223> OTHER INFORMATION: transmembrane domain mouse ST6GalII

<400> SEQUENCE: 8

Met Leu Phe Gly Ile Phe Val Trp Gly Leu Leu Phe Leu Ala Ile Phe
1               5                   10                  15

Ile Tyr Phe Thr Asn
            20

<210> SEQ ID NO 9
<211> LENGTH: 21
<212> TYPE: PRT
<213> ORGANISM: Artificial Sequence
<220> FEATURE:
<223> OTHER INFORMATION: TMD rat ST6GalII

<400> SEQUENCE: 9

Met Leu Phe Ala Ile Phe Val Trp Gly Leu Leu Phe Leu Ala Ile Phe
1               5                   10                  15

Ile Tyr Phe Thr Asn
            20

<210> SEQ ID NO 10
<211> LENGTH: 20
<212> TYPE: PRT
<213> ORGANISM: Artificial Sequence
<220> FEATURE:
<223> OTHER INFORMATION: TMD human ST3GalIII

<400> SEQUENCE: 10

Asn Leu Leu Leu Ala Leu Cys Leu Phe Leu Val Leu Gly Phe Leu Tyr
1               5                   10                  15

Tyr Ser Ala Trp
            20

<210> SEQ ID NO 11
<211> LENGTH: 20
<212> TYPE: PRT
<213> ORGANISM: Artificial Sequence
<220> FEATURE:
<223> OTHER INFORMATION: TMD CHO ST3GalIII

<400> SEQUENCE: 11

Asn Leu Leu Leu Ala Leu Cys Leu Phe Leu Val Leu Gly Phe Leu Tyr
1               5                   10                  15

Tyr Ser Ala Trp
            20

<210> SEQ ID NO 12
<211> LENGTH: 20
<212> TYPE: PRT
<213> ORGANISM: Artificial Sequence
<220> FEATURE:
<223> OTHER INFORMATION: TMD mouse ST3GalIII

<400> SEQUENCE: 12

Asn Leu Leu Leu Ala Leu Cys Leu Phe Leu Val Leu Gly Phe Leu Tyr
1               5                   10                  15

Tyr Ser Ala Trp
            20
```

<210> SEQ ID NO 13
<211> LENGTH: 20
<212> TYPE: PRT
<213> ORGANISM: Artificial Sequence
<220> FEATURE:
<223> OTHER INFORMATION: TMD rat ST3GalIII

<400> SEQUENCE: 13

Asn Leu Leu Leu Ala Leu Cys Leu Phe Leu Val Leu Gly Phe Leu Tyr
1               5                   10                  15

Tyr Ser Ala Trp
            20

<210> SEQ ID NO 14
<211> LENGTH: 13
<212> TYPE: PRT
<213> ORGANISM: Artificial Sequence
<220> FEATURE:
<223> OTHER INFORMATION: TMD human ST8SiaIV

<400> SEQUENCE: 14

Trp Thr Ile Cys Thr Ile Ser Leu Leu Leu Ile Phe Tyr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: TMD mouse ST8SiaIV

<400> SEQUENCE: 15

Trp Thr Ile Cys Thr Ile Ser Leu Leu Leu Ile Phe Tyr
1               5                   10

<210> SEQ ID NO 16
<211> LENGTH: 13
<212> TYPE: PRT
<213> ORGANISM: Artificial Sequence
<220> FEATURE:
<223> OTHER INFORMATION: TMD rat ST8SiaIV

<400> SEQUENCE: 16

Trp Thr Ile Cys Thr Ile Ser Leu Leu Leu Ile Phe Tyr
1               5                   10

<210> SEQ ID NO 17
<211> LENGTH: 54
<212> TYPE: PRT
<213> ORGANISM: Artificial Sequence
<220> FEATURE:
<223> OTHER INFORMATION: SR (stem region) human ST6GalI

<400> SEQUENCE: 17

Asp Ser Phe Lys Leu Gln Thr Lys Glu Phe Gln Val Leu Lys Ser Leu
1               5                   10                  15

Gly Lys Leu Ala Met Gly Ser Asp Ser Gln Ser Val Ser Ser Ser Ser
            20                  25                  30

Thr Gln Asp Pro His Arg Gly Arg Gln Thr Leu Gly Ser Leu Arg Gly
        35                  40                  45

Leu Ala Lys Ala Lys Pro
    50

```
<210> SEQ ID NO 18
<211> LENGTH: 54
<212> TYPE: PRT
<213> ORGANISM: Artificial Sequence
<220> FEATURE:
<223> OTHER INFORMATION: SR CHO ST6GalI

<400> SEQUENCE: 18

Glu Ala Leu Lys Leu Gln Ala Lys Glu Phe Gln Val Thr Arg Ser Leu
1               5                   10                  15

Glu Lys Leu Ala Met Arg Ser Gly Ser Gln Ser Met Ser Ser Ser
            20                  25                  30

Lys Gln Asp Pro Lys Gln Asp Ser Gln Val Leu Ser His Ala Arg Val
        35                  40                  45

Thr Ala Lys Val Lys Pro
    50

<210> SEQ ID NO 19
<211> LENGTH: 53
<212> TYPE: PRT
<213> ORGANISM: Artificial Sequence
<220> FEATURE:
<223> OTHER INFORMATION: SR mouse ST6GalI

<400> SEQUENCE: 19

Glu Ala Leu Thr Leu Gln Ala Lys Val Phe Gln Met Pro Lys Ser Gln
1               5                   10                  15

Glu Lys Val Ala Val Gly Pro Ala Pro Ala Val Phe Ser Asn Ser Lys
            20                  25                  30

Gln Asp Pro Lys Glu Gly Val Gln Ile Leu Ser Tyr Pro Arg Val Thr
        35                  40                  45

Ala Lys Val Lys Pro
    50

<210> SEQ ID NO 20
<211> LENGTH: 54
<212> TYPE: PRT
<213> ORGANISM: Artificial Sequence
<220> FEATURE:
<223> OTHER INFORMATION: SR rat ST6GalI

<400> SEQUENCE: 20

Glu Ala Leu Thr Leu Gln Ala Lys Glu Phe Gln Met Pro Lys Ser Gln
1               5                   10                  15

Glu Lys Val Ala Met Gly Ser Ala Ser Gln Val Val Phe Ser Asn Ser
            20                  25                  30

Lys Gln Asp Pro Lys Glu Asp Ile Pro Ile Leu Ser Tyr His Arg Val
        35                  40                  45

Thr Ala Lys Val Lys Pro
    50

<210> SEQ ID NO 21
<211> LENGTH: 53
<212> TYPE: PRT
<213> ORGANISM: Artificial Sequence
<220> FEATURE:
<223> OTHER INFORMATION: SR human ST6GalII

<400> SEQUENCE: 21

Ser Asn Pro Ala Glu Pro Val Pro Ser Ser Leu Ser Phe Leu Glu Thr
1               5                   10                  15

Arg Arg Leu Leu Pro Val Gln Gly Lys Gln Arg Ala Ile Met Gly Ala
```

```
                    20                  25                  30

Ala His Glu Pro Ser Pro Gly Gly Leu Asp Ala Arg Gln Ala Leu
            35                  40                  45

Pro Arg Ala His Pro
    50

<210> SEQ ID NO 22
<211> LENGTH: 53
<212> TYPE: PRT
<213> ORGANISM: Artificial Sequence
<220> FEATURE:
<223> OTHER INFORMATION: SR CHO ST6GalII

<400> SEQUENCE: 22

Ser Asn Pro Ala Ser Pro Val Pro Ser Ser Phe Ser Phe Val Glu Asn
1               5                   10                  15

Arg Gly Leu Leu Pro Val Gln Gly Lys Gln Arg Ala Ile Met Gly Ala
            20                  25                  30

Leu Gln Glu Ser Ser Leu Pro Arg Ser Leu Glu Ala Ser Lys Ala Leu
        35                  40                  45

Pro Gly Ser His Pro
    50

<210> SEQ ID NO 23
<211> LENGTH: 53
<212> TYPE: PRT
<213> ORGANISM: Artificial Sequence
<220> FEATURE:
<223> OTHER INFORMATION: SR mouse ST6GalII

<400> SEQUENCE: 23

Ser Asn Pro Ala Ala Pro Met Pro Ser Ser Phe Ser Phe Leu Glu Ser
1               5                   10                  15

Arg Gly Leu Leu Pro Leu Gln Gly Lys Gln Arg Val Ile Met Gly Ala
            20                  25                  30

Leu Gln Glu Pro Ser Leu Pro Arg Ser Leu Asp Ala Ser Lys Val Leu
        35                  40                  45

Leu Asp Ser His Pro
    50

<210> SEQ ID NO 24
<211> LENGTH: 53
<212> TYPE: PRT
<213> ORGANISM: Artificial Sequence
<220> FEATURE:
<223> OTHER INFORMATION: SR rat ST6GalII

<400> SEQUENCE: 24

Ser Asn Pro Ala Ala Pro Met Pro Ser Ser Phe Ser Phe Leu Glu Ser
1               5                   10                  15

Arg Gly Leu Leu Pro Val Gln Gly Lys Gln Arg Val Ile Met Gly Ala
            20                  25                  30

Leu Gln Glu Pro Ser Leu Pro Arg Ser Leu Glu Pro Ser Lys Val Leu
        35                  40                  45

Met Asp Gly His Ser
    50

<210> SEQ ID NO 25
<211> LENGTH: 18
<212> TYPE: PRT
<213> ORGANISM: Artificial Sequence
```

```
<220> FEATURE:
<223> OTHER INFORMATION: SR human ST3GalIII

<400> SEQUENCE: 25

Lys Leu His Leu Leu Gln Trp Glu Glu Asp Ser Asn Ser Val Val Leu
1               5                   10                  15

Ser Phe

<210> SEQ ID NO 26
<211> LENGTH: 17
<212> TYPE: PRT
<213> ORGANISM: Artificial Sequence
<220> FEATURE:
<223> OTHER INFORMATION: SR CHO ST3GalIII

<400> SEQUENCE: 26

Lys Leu His Leu Leu Gln Trp Glu Asp Ser Asn Ser Leu Leu Leu Ser
1               5                   10                  15

Leu

<210> SEQ ID NO 27
<211> LENGTH: 17
<212> TYPE: PRT
<213> ORGANISM: Artificial Sequence
<220> FEATURE:
<223> OTHER INFORMATION: SR mouse ST3GalIII

<400> SEQUENCE: 27

Lys Leu His Leu Leu Gln Trp Glu Asp Ser Asn Ser Leu Leu Leu Ser
1               5                   10                  15

Leu

<210> SEQ ID NO 28
<211> LENGTH: 17
<212> TYPE: PRT
<213> ORGANISM: Artificial Sequence
<220> FEATURE:
<223> OTHER INFORMATION: SR rat ST3GalIII

<400> SEQUENCE: 28

Lys Leu His Leu Leu Gln Trp Glu Asp Ser Asn Ser Leu Ile Leu Ser
1               5                   10                  15

Leu

<210> SEQ ID NO 29
<211> LENGTH: 47
<212> TYPE: PRT
<213> ORGANISM: Artificial Sequence
<220> FEATURE:
<223> OTHER INFORMATION: SR human ST8SiaIV

<400> SEQUENCE: 29

Lys Thr Lys Glu Ile Ala Arg Thr Glu Glu His Gln Glu Thr Gln Leu
1               5                   10                  15

Ile Gly Asp Gly Glu Leu Ser Leu Ser Arg Ser Leu Val Asn Ser Ser
                20                  25                  30

Asp Lys Ile Ile Arg Lys Ala Gly Ser Ser Ile Phe Gln His Asn
            35                  40                  45

<210> SEQ ID NO 30
<211> LENGTH: 47
<212> TYPE: PRT
<213> ORGANISM: Artificial Sequence
```

```
<220> FEATURE:
<223> OTHER INFORMATION: SR mouse ST8SiaIV

<400> SEQUENCE: 30

Lys Thr Lys Glu Ile Ala Arg Thr Glu Glu His Gln Glu Thr Gln Leu
1               5                   10                  15

Ile Gly Asp Gly Glu Leu Cys Leu Ser Arg Ser Leu Val Asn Ser Ser
            20                  25                  30

Asp Lys Ile Ile Arg Lys Ala Gly Ser Thr Ile Phe Gln His Ser
        35                  40                  45

<210> SEQ ID NO 31
<211> LENGTH: 47
<212> TYPE: PRT
<213> ORGANISM: Artificial Sequence
<220> FEATURE:
<223> OTHER INFORMATION: SR rat ST8SiaIV

<400> SEQUENCE: 31

Lys Thr Lys Glu Ile Ala Arg Thr Glu Glu His Gln Glu Thr Gln Leu
1               5                   10                  15

Ile Gly Asp Gly Glu Leu Cys Leu Ser Arg Ser Leu Val Asn Asn Ser
            20                  25                  30

Asp Lys Ile Thr Arg Lys Ala Gly Ser Thr Ile Phe Gln His Ser
        35                  40                  45

<210> SEQ ID NO 32
<211> LENGTH: 56
<212> TYPE: PRT
<213> ORGANISM: Artificial Sequence
<220> FEATURE:
<223> OTHER INFORMATION: SR human ST8SiaII

<400> SEQUENCE: 32

Asp Ile Ser Glu Ile Glu Glu Ile Gly Asn Ser Gly Gly Arg Gly
1               5                   10                  15

Thr Ile Arg Ser Ala Val Asn Ser Leu His Ser Lys Ser Asn Arg Ala
            20                  25                  30

Glu Val Val Ile Asn Gly Ser Ser Pro Ala Val Val Asp Arg Ser
        35                  40                  45

Asn Glu Ser Ile Lys His Asn Ile
    50                  55

<210> SEQ ID NO 33
<211> LENGTH: 56
<212> TYPE: PRT
<213> ORGANISM: Artificial Sequence
<220> FEATURE:
<223> OTHER INFORMATION: SR mouse ST8SiaII

<400> SEQUENCE: 33

Asp Ile Ser Glu Ile Glu Glu Ile Gly Asn Ser Gly Gly Arg Gly
1               5                   10                  15

Thr Ile Arg Ser Ala Val Asn Ser Leu His Ser Lys Ser Asn Arg Ala
            20                  25                  30

Glu Val Val Ile Asn Gly Ser Pro Pro Ala Val Ala Asp Arg Ser
        35                  40                  45

Asn Glu Ser Leu Lys His Asn Ile
    50                  55

<210> SEQ ID NO 34
```

```
<211> LENGTH: 56
<212> TYPE: PRT
<213> ORGANISM: Artificial Sequence
<220> FEATURE:
<223> OTHER INFORMATION: SR rat ST8SiaII

<400> SEQUENCE: 34

Asp Ile Ser Glu Ile Glu Glu Ile Gly Asn Ser Gly Gly Arg Gly
 1               5                  10                  15

Thr Ile Arg Ser Ala Val Asn Ser Leu His Ser Lys Ser Asn Arg Ala
            20                  25                  30

Glu Val Val Ile Asn Gly Ser Ser Leu Pro Ala Val Ala Asp Arg Ser
        35                  40                  45

Asn Glu Ser Leu Lys His Ser Ile
    50                  55

<210> SEQ ID NO 35
<211> LENGTH: 402
<212> TYPE: PRT
<213> ORGANISM: Artificial Sequence
<220> FEATURE:
<223> OTHER INFORMATION: Anchor sequence of ST6Gal1 of CHO and Catalytic
      domain of human ST6Gal1

<400> SEQUENCE: 35

Met Ile His Thr Asn Leu Lys Lys Phe Ser Tyr Phe Ile Leu Ala
 1               5                  10                  15

Phe Leu Leu Phe Ala Leu Ile Cys Val Trp Lys Lys Gly Ser Tyr Glu
            20                  25                  30

Ala Leu Lys Leu Gln Ala Lys Glu Phe Gln Val Thr Arg Ser Leu Glu
        35                  40                  45

Lys Leu Ala Met Arg Ser Gly Ser Gln Ser Met Ser Ser Ser Ser Lys
    50                  55                  60

Gln Asp Pro Lys Gln Asp Ser Gln Val Leu Ser His Ala Arg Val Thr
65                  70                  75                  80

Ala Lys Val Lys Pro Glu Ala Ser Phe Gln Val Trp Asn Lys Asp Ser
                85                  90                  95

Ser Ser Lys Asn Leu Ile Pro Arg Leu Gln Lys Ile Trp Lys Asn Tyr
            100                 105                 110

Leu Ser Met Asn Lys Tyr Lys Val Ser Tyr Lys Gly Pro Gly Pro Gly
        115                 120                 125

Ile Lys Phe Ser Ala Glu Ala Leu Arg Cys His Leu Arg Asp His Val
    130                 135                 140

Asn Val Ser Met Val Glu Val Thr Asp Phe Pro Phe Asn Thr Ser Glu
145                 150                 155                 160

Trp Glu Gly Tyr Leu Pro Lys Glu Ser Ile Arg Thr Lys Ala Gly Pro
                165                 170                 175

Trp Gly Arg Cys Ala Val Val Ser Ser Ala Gly Ser Leu Lys Ser Ser
            180                 185                 190

Gln Leu Gly Arg Glu Ile Asp Asp His Asp Ala Val Leu Arg Phe Asn
        195                 200                 205

Gly Ala Pro Thr Ala Asn Phe Gln Gln Asp Val Gly Thr Lys Thr Thr
    210                 215                 220

Ile Arg Leu Met Asn Ser Gln Leu Val Thr Thr Glu Lys Arg Phe Leu
225                 230                 235                 240

Lys Asp Ser Leu Tyr Asn Glu Gly Ile Leu Ile Val Trp Asp Pro Ser
                245                 250                 255
```

Val Tyr His Ser Asp Ile Pro Lys Trp Tyr Gln Asn Pro Asp Tyr Asn
                260                 265                 270

Phe Phe Asn Asn Tyr Lys Thr Tyr Arg Lys Leu His Pro Asn Gln Pro
            275                 280                 285

Phe Tyr Ile Leu Lys Pro Gln Met Pro Trp Glu Leu Trp Asp Ile Leu
        290                 295                 300

Gln Glu Ile Ser Pro Glu Glu Ile Gln Pro Asn Pro Pro Ser Ser Gly
305                 310                 315                 320

Met Leu Gly Ile Ile Ile Met Met Thr Leu Cys Asp Gln Val Asp Ile
                325                 330                 335

Tyr Glu Phe Leu Pro Ser Lys Arg Lys Thr Asp Val Cys Tyr Tyr Tyr
            340                 345                 350

Gln Lys Phe Phe Asp Ser Ala Cys Thr Met Gly Ala Tyr His Pro Leu
        355                 360                 365

Leu Tyr Glu Lys Asn Leu Val Lys His Leu Asn Gln Gly Thr Asp Glu
    370                 375                 380

Asp Ile Tyr Leu Leu Gly Lys Ala Thr Leu Pro Gly Phe Arg Thr Ile
385                 390                 395                 400

His Cys

<210> SEQ ID NO 36
<211> LENGTH: 406
<212> TYPE: PRT
<213> ORGANISM: Artificial Sequence
<220> FEATURE:
<223> OTHER INFORMATION: Anchor sequence of human ST8Sia2 and Catalytic
      domain of human ST6Gal1

<400> SEQUENCE: 36

Met Asp Tyr Lys Asp Asp Asp Lys Gln Leu Gln Phe Arg Ser Trp
1               5                   10                  15

Met Leu Ala Ala Leu Thr Leu Leu Val Val Phe Leu Ile Phe Ala Asp
                20                  25                  30

Ile Ser Glu Ile Glu Glu Ile Gly Asn Ser Gly Gly Arg Gly Thr
            35                  40                  45

Ile Arg Ser Ala Val Asn Ser Leu His Ser Lys Ser Asn Arg Ala Glu
    50                  55                  60

Val Val Ile Asn Gly Ser Ser Pro Ala Val Val Asp Arg Ser Asn
65                  70                  75                  80

Glu Ser Ile Lys His Asn Ile Lys Leu Glu Ala Ser Phe Gln Val Trp
                85                  90                  95

Asn Lys Asp Ser Ser Lys Asn Leu Ile Pro Arg Leu Gln Lys Ile
            100                 105                 110

Trp Lys Asn Tyr Leu Ser Met Asn Lys Tyr Lys Val Ser Tyr Lys Gly
        115                 120                 125

Pro Gly Pro Gly Ile Lys Phe Ser Ala Glu Ala Leu Arg Cys His Leu
    130                 135                 140

Arg Asp His Val Asn Val Ser Met Val Glu Val Thr Asp Phe Pro Phe
145                 150                 155                 160

Asn Thr Ser Glu Trp Glu Gly Tyr Leu Pro Lys Glu Ser Ile Arg Thr
                165                 170                 175

Lys Ala Gly Pro Trp Gly Arg Cys Ala Val Val Ser Ser Ala Gly Ser
            180                 185                 190

Leu Lys Ser Ser Gln Leu Gly Arg Glu Ile Asp Asp His Asp Ala Val
        195                 200                 205

```
Leu Arg Phe Asn Gly Ala Pro Thr Ala Asn Phe Gln Gln Asp Val Gly
    210                 215                 220

Thr Lys Thr Thr Ile Arg Leu Met Asn Ser Gln Leu Val Thr Thr Glu
225                 230                 235                 240

Lys Arg Phe Leu Lys Asp Ser Leu Tyr Asn Glu Gly Ile Leu Ile Val
                    245                 250                 255

Trp Asp Pro Ser Val Tyr His Ser Asp Ile Pro Lys Trp Tyr Gln Asn
                260                 265                 270

Pro Asp Tyr Asn Phe Phe Asn Asn Tyr Lys Thr Tyr Arg Lys Leu His
            275                 280                 285

Pro Asn Gln Pro Phe Tyr Ile Leu Lys Pro Gln Met Pro Trp Glu Leu
        290                 295                 300

Trp Asp Ile Leu Gln Glu Ile Ser Pro Glu Glu Ile Gln Pro Asn Pro
305                 310                 315                 320

Pro Ser Ser Gly Met Leu Gly Ile Ile Ile Met Met Thr Leu Cys Asp
                    325                 330                 335

Gln Val Asp Ile Tyr Glu Phe Leu Pro Ser Lys Arg Lys Thr Asp Val
                340                 345                 350

Cys Tyr Tyr Tyr Gln Lys Phe Phe Asp Ser Ala Cys Thr Met Gly Ala
            355                 360                 365

Tyr His Pro Leu Leu Tyr Glu Lys Asn Leu Val Lys His Leu Asn Gln
        370                 375                 380

Gly Thr Asp Glu Asp Ile Tyr Leu Leu Gly Lys Ala Thr Leu Pro Gly
385                 390                 395                 400

Phe Arg Thr Ile His Cys
                405

<210> SEQ ID NO 37
<211> LENGTH: 420
<212> TYPE: PRT
<213> ORGANISM: Artificial Sequence
<220> FEATURE:
<223> OTHER INFORMATION: preprotrypsinogen signal sequence, a Flag-Tag,
      the anchor sequence of the human ST8Sia2 fused to the catalytic
      domain of the human ST6Gal1

<400> SEQUENCE: 37

Met Ser Ala Leu Leu Ile Leu Ala Leu Val Gly Ala Ala Val Ala Asp
1               5                   10                  15

Tyr Lys Asp Asp Asp Asp Lys Gln Leu Gln Phe Arg Ser Trp Met Leu
                20                  25                  30

Ala Ala Leu Thr Leu Leu Val Val Phe Leu Ile Phe Ala Asp Ile Ser
            35                  40                  45

Glu Ile Glu Glu Glu Ile Gly Asn Ser Gly Gly Arg Gly Thr Ile Arg
50                  55                  60

Ser Ala Val Asn Ser Leu His Ser Lys Ser Asn Arg Ala Glu Val Val
65                  70                  75                  80

Ile Asn Gly Ser Ser Ser Pro Ala Val Val Asp Arg Ser Asn Glu Ser
                    85                  90                  95

Ile Lys His Asn Ile Lys Leu Glu Ala Ser Phe Gln Val Trp Asn Lys
                100                 105                 110

Asp Ser Ser Ser Lys Asn Leu Ile Pro Arg Leu Gln Lys Ile Trp Lys
            115                 120                 125

Asn Tyr Leu Ser Met Asn Lys Tyr Lys Val Ser Tyr Lys Gly Pro Gly
        130                 135                 140

Pro Gly Ile Lys Phe Ser Ala Glu Ala Leu Arg Cys His Leu Arg Asp
```

-continued

```
               145                 150                 155                 160
        His Val Asn Val Ser Met Val Glu Val Thr Asp Phe Pro Phe Asn Thr
                        165                 170                 175

Ser Glu Trp Glu Gly Tyr Leu Pro Lys Glu Ser Ile Arg Thr Lys Ala
                        180                 185                 190

Gly Pro Trp Gly Arg Cys Ala Val Ser Ser Ala Gly Ser Leu Lys
                        195                 200                 205

Ser Ser Gln Leu Gly Arg Glu Ile Asp Asp His Asp Ala Val Leu Arg
            210                 215                 220

Phe Asn Gly Ala Pro Thr Ala Asn Phe Gln Gln Asp Val Gly Thr Lys
        225                 230                 235                 240

Thr Thr Ile Arg Leu Met Asn Ser Gln Leu Val Thr Thr Glu Lys Arg
                        245                 250                 255

Phe Leu Lys Asp Ser Leu Tyr Asn Glu Gly Ile Leu Ile Val Trp Asp
                        260                 265                 270

Pro Ser Val Tyr His Ser Asp Ile Pro Lys Trp Tyr Gln Asn Pro Asp
                        275                 280                 285

Tyr Asn Phe Phe Asn Asn Tyr Lys Thr Tyr Arg Lys Leu His Pro Asn
            290                 295                 300

Gln Pro Phe Tyr Ile Leu Lys Pro Gln Met Pro Trp Glu Leu Trp Asp
        305                 310                 315                 320

Ile Leu Gln Glu Ile Ser Pro Glu Glu Ile Gln Pro Asn Pro Pro Ser
                        325                 330                 335

Ser Gly Met Leu Gly Ile Ile Ile Met Met Thr Leu Cys Asp Gln Val
                        340                 345                 350

Asp Ile Tyr Glu Phe Leu Pro Ser Lys Arg Lys Thr Asp Val Cys Tyr
                        355                 360                 365

Tyr Tyr Gln Lys Phe Phe Asp Ser Ala Cys Thr Met Gly Ala Tyr His
                        370                 375                 380

Pro Leu Leu Tyr Glu Lys Asn Leu Val Lys His Leu Asn Gln Gly Thr
        385                 390                 395                 400

Asp Glu Asp Ile Tyr Leu Leu Gly Lys Ala Thr Leu Pro Gly Phe Arg
                        405                 410                 415

Thr Ile His Cys
                    420

<210> SEQ ID NO 38
<211> LENGTH: 373
<212> TYPE: PRT
<213> ORGANISM: Artificial Sequence
<220> FEATURE:
<223> OTHER INFORMATION: Anchor sequence of human ST3Gal3 and Catalytic
      domain of human ST6Gal1

<400> SEQUENCE: 38

Met Asp Tyr Lys Asp Asp Asp Lys Gly Leu Leu Val Phe Val Arg
        1               5                   10                  15

Asn Leu Leu Leu Ala Leu Cys Leu Phe Leu Val Leu Gly Phe Leu Tyr
                        20                  25                  30

Tyr Ser Ala Trp Lys Leu His Leu Leu Gln Trp Glu Glu Asp Ser Ser
                        35                  40                  45

Lys Tyr Ser His Ser Ser Gly Ser Glu Ala Ser Phe Gln Val Trp Asn
            50                  55                  60

Lys Asp Ser Ser Ser Lys Asn Leu Ile Pro Arg Leu Gln Lys Ile Trp
        65                  70                  75                  80
```

Lys Asn Tyr Leu Ser Met Asn Lys Tyr Lys Val Ser Tyr Lys Gly Pro
            85                  90                  95

Gly Pro Gly Ile Lys Phe Ser Ala Glu Ala Leu Arg Cys His Leu Arg
            100                 105                 110

Asp His Val Asn Val Ser Met Val Glu Val Thr Asp Phe Pro Phe Asn
            115                 120                 125

Thr Ser Glu Trp Glu Gly Tyr Leu Pro Lys Glu Ser Ile Arg Thr Lys
            130                 135                 140

Ala Gly Pro Trp Gly Arg Cys Ala Val Val Ser Ser Ala Gly Ser Leu
145                 150                 155                 160

Lys Ser Ser Gln Leu Gly Arg Glu Ile Asp Asp His Asp Ala Val Leu
            165                 170                 175

Arg Phe Asn Gly Ala Pro Thr Ala Asn Phe Gln Gln Asp Val Gly Thr
            180                 185                 190

Lys Thr Thr Ile Arg Leu Met Asn Ser Gln Leu Val Thr Thr Glu Lys
            195                 200                 205

Arg Phe Leu Lys Asp Ser Leu Tyr Asn Glu Gly Ile Leu Ile Val Trp
            210                 215                 220

Asp Pro Ser Val Tyr His Ser Asp Ile Pro Lys Trp Tyr Gln Asn Pro
225                 230                 235                 240

Asp Tyr Asn Phe Phe Asn Asn Tyr Lys Thr Tyr Arg Lys Leu His Pro
            245                 250                 255

Asn Gln Pro Phe Tyr Ile Leu Lys Pro Gln Met Pro Trp Glu Leu Trp
            260                 265                 270

Asp Ile Leu Gln Glu Ile Ser Pro Glu Glu Ile Gln Pro Asn Pro Pro
            275                 280                 285

Ser Ser Gly Met Leu Gly Ile Ile Ile Met Met Thr Leu Cys Asp Gln
290                 295                 300

Val Asp Ile Tyr Glu Phe Leu Pro Ser Lys Arg Lys Thr Asp Val Cys
305                 310                 315                 320

Tyr Tyr Tyr Gln Lys Phe Phe Asp Ser Ala Cys Thr Met Gly Ala Tyr
            325                 330                 335

His Pro Leu Leu Tyr Glu Lys Asn Leu Val Lys His Leu Asn Gln Gly
            340                 345                 350

Thr Asp Glu Asp Ile Tyr Leu Leu Gly Lys Ala Thr Leu Pro Gly Phe
            355                 360                 365

Arg Thr Ile His Cys
            370

<210> SEQ ID NO 39
<211> LENGTH: 391
<212> TYPE: PRT
<213> ORGANISM: Artificial Sequence
<220> FEATURE:
<223> OTHER INFORMATION: cytoplasmic domain of human ST3Gal3, the
      transmembrane domain of human ST8Sia2, and the stem region of
      human ST8Sia2 fused to the catalytic domain of the human ST6Gal1

<400> SEQUENCE: 39

Met Asp Tyr Lys Asp Asp Asp Lys Gly Leu Leu Val Phe Val Arg
1               5                   10                  15

Ser Trp Met Leu Ala Ala Leu Thr Leu Leu Val Val Phe Leu Ile Phe
            20                  25                  30

Ala Lys Glu Pro Gln Thr Lys Pro Ser Arg His Gln Arg Thr Glu Asn
            35                  40                  45

Ile Lys Glu Arg Ser Leu Gln Ser Leu Ala Lys Pro Lys Ser Gln Ala

```
             50                   55                   60
Pro Thr Arg Ala Arg Arg Thr Thr Gly Ser Glu Ala Ser Phe Gln Val
 65                   70                   75                   80

Trp Asn Lys Asp Ser Ser Lys Asn Leu Ile Pro Arg Leu Gln Lys
                     85                   90                   95

Ile Trp Lys Asn Tyr Leu Ser Met Asn Lys Tyr Lys Val Ser Tyr Lys
                    100                  105                  110

Gly Pro Gly Pro Gly Ile Lys Phe Ser Ala Glu Ala Leu Arg Cys His
                    115                  120                  125

Leu Arg Asp His Val Asn Val Ser Met Val Glu Val Thr Asp Phe Pro
                130                  135                  140

Phe Asn Thr Ser Glu Trp Glu Gly Tyr Leu Pro Lys Glu Ser Ile Arg
145                  150                  155                  160

Thr Lys Ala Gly Pro Trp Gly Arg Cys Ala Val Val Ser Ser Ala Gly
                    165                  170                  175

Ser Leu Lys Ser Ser Gln Leu Gly Arg Glu Ile Asp Asp His Asp Ala
                180                  185                  190

Val Leu Arg Phe Asn Gly Ala Pro Thr Ala Asn Phe Gln Gln Asp Val
                195                  200                  205

Gly Thr Lys Thr Thr Ile Arg Leu Met Asn Ser Gln Leu Val Thr Thr
210                  215                  220

Glu Lys Arg Phe Leu Lys Asp Ser Leu Tyr Asn Glu Gly Ile Leu Ile
225                  230                  235                  240

Val Trp Asp Pro Ser Val Tyr His Ser Asp Ile Pro Lys Trp Tyr Gln
                    245                  250                  255

Asn Pro Asp Tyr Asn Phe Phe Asn Asn Tyr Lys Thr Tyr Arg Lys Leu
                260                  265                  270

His Pro Asn Gln Pro Phe Tyr Ile Leu Lys Pro Gln Met Pro Trp Glu
                275                  280                  285

Leu Trp Asp Ile Leu Gln Glu Ile Ser Pro Glu Glu Ile Gln Pro Asn
                290                  295                  300

Pro Pro Ser Ser Gly Met Leu Gly Ile Ile Ile Met Met Thr Leu Cys
305                  310                  315                  320

Asp Gln Val Asp Ile Tyr Glu Phe Leu Pro Ser Lys Arg Lys Thr Asp
                    325                  330                  335

Val Cys Tyr Tyr Tyr Gln Lys Phe Phe Asp Ser Ala Cys Thr Met Gly
                340                  345                  350

Ala Tyr His Pro Leu Leu Tyr Glu Lys Asn Leu Val Lys His Leu Asn
                355                  360                  365

Gln Gly Thr Asp Glu Asp Ile Tyr Leu Leu Gly Lys Ala Thr Leu Pro
                370                  375                  380

Gly Phe Arg Thr Ile His Cys
385                  390

<210> SEQ ID NO 40
<211> LENGTH: 683
<212> TYPE: DNA
<213> ORGANISM: Artificial Sequence
<220> FEATURE:
<223> OTHER INFORMATION: Fc IgG1

<400> SEQUENCE: 40
gcgacaagac ccacacctgt ccccttgtc ctgcccctga actgctgggc ggacccagcg      60
tgttcctgtt ccccccaaag cccaaggaca ccctcatgat ctcccggacc cctgaggtca    120
```

| | |
|---|---|
| catgcgtggt ggtggacgtg agccacgaag accctgaggt caagttcaac tggtacgtgg | 180 |
| acggcgtgga ggtgcataat gccaagacaa agccgcggga ggagcagtac aacagcacgt | 240 |
| accgtgtggt cagcgtcctc accgtcctgc accaggactg gctgaatggc aaggagtaca | 300 |
| agtgcaaggt ctccaacaaa gccctcccag ccccatcga gaaaaccatc tccaaagcca | 360 |
| aagggcagcc ccgagaacca caggtgtaca ccctgccccc atcccgggag gagatgacca | 420 |
| agaaccaggt cagcctgacc tgcctggtca aaggcttcta tcccagcgac atcgccgtgg | 480 |
| agtgggagag caatgggcag ccggagaaca actacaagac cacgcctccc gtgctggact | 540 |
| ccgacggctc cttcttcctc tacagcaagc tcaccgtgga caagagcagg tggcagcagg | 600 |
| ggaacgtctt ctcatgctcc gtgatgcacg aggctctgca caaccactac acgcagaaga | 660 |
| gcctctccct gtctccgggt aaa | 683 |

<210> SEQ ID NO 41
<211> LENGTH: 1413
<212> TYPE: DNA
<213> ORGANISM: Artificial Sequence
<220> FEATURE:
<223> OTHER INFORMATION: Heavy chain of Inflixilmab

<400> SEQUENCE: 41

| | |
|---|---|
| atgtacagga tgcaactcct gtcttgcatt gcactaagtc ttgcacttgt cacgaattcg | 60 |
| gaagtgaagc tggaagagtc cggcggaggc ctggtgcagc ctggcggatc tatgaagctg | 120 |
| tcctgcgtgg cctccggctt catcttctcc aaccactgga tgaactgggt gcgacagtcc | 180 |
| cccgagaagg cctggaatg ggtggccgag atccggtcca agtccatcaa ctccgccacc | 240 |
| cactacgccg agtctgtgaa gggccggttc accatctccc gggacgactc caagtccgcc | 300 |
| gtgtacctgc agatgaccga cctgagaacc gaggacaccg cgtgtacta ctgctcccgg | 360 |
| aactactacg gctccaccta cgactactgg ggccagggca ccaccctgac cgtgtctgct | 420 |
| gcttctacca agggccctc cgtgttccct ctggcccctt ccagcaagtc tacctctggc | 480 |
| ggcacagccg ctctgggctg cctcgtgaag gactacttcc ccgagcccgt gacagtgtcc | 540 |
| tggaactctg gcgctctgac ctccggcgtg cacacctttc cagctgtgct gcagtcctcc | 600 |
| ggcctgtact ccctgtcctc cgtcgtgacc gtgccttcca gctctctggg cacccagacc | 660 |
| tacatctgca acgtgaacca caagccctcc aacaccaagg tggacaagaa ggtgaaccc | 720 |
| aagtcctgcg acaagaccca cacctgtccc ccttgtcctg cccctgaact gctgggcgga | 780 |
| cccagcgtgt tcctgttccc cccaaagccc aaggacaccc tcatgatctc ccggacccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag ggcagccccg agaaccacag gtgtacaccc tgcccccatc ccgggaggag | 1140 |
| atgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctac agcaagctca ccgtggacaa gagcaggtgg | 1320 |
| cagcagggga acgtcttctc atgctccgtg atgcacgagg ctctgcacaa ccactacacg | 1380 |
| cagaagagcc tctccctgtc tccgggtaaa tga | 1413 |

```
<210> SEQ ID NO 42
<211> LENGTH: 708
<212> TYPE: DNA
<213> ORGANISM: Artificial Sequence
<220> FEATURE:
<223> OTHER INFORMATION: Light chain Infliximab

<400> SEQUENCE: 42
atgtacagga tgcaactcct gtcttgcatt gcactaagtc ttgcacttgt cacgaattcg      60
gacatcctgc tgacccagtc ccccgccatc ctgagtgtgt ctccaggcga gcgggtgtcc     120
ttctcttgtc gggcctctca gttcgtgggc tcctccatcc actggtatca gcagcggacc     180
aacggctccc ctcggctgct gattaagtac gcctccgagt ctatgtccgg catcccctcc     240
agattctccg gctctggctc tggcaccgac ttcaccctgt ccatcaacac cgtggaatcc     300
gaggatatcg ccgactacta ctgccagcag tcccactcct ggcccttcac cttcggctcc     360
ggcaccaacc tggaagtgaa agaaccgtg gccgctccct ccgtgttcat cttcccacct     420
tccgacgagc agctgaagtc cggcaccgct tctgtcgtgt gcctgctgaa caacttctac     480
ccccgcgagg ccaaggtgca gtggaaggtg gacaacgccc tgcagtccgg caactcccag     540
gaatccgtga ccgagcagga ctccaaggac agcacctact ccctgtcctc caccctgacc     600
ctgagcaagg ccgactacga aagcacaag gtgtacgcct gcgaagtgac ccaccagggc     660
ctgtctagcc ccgtgaccaa gtctttcaac cggggcgagt gctgatga                708

<210> SEQ ID NO 43
<211> LENGTH: 336
<212> TYPE: PRT
<213> ORGANISM: Artificial Sequence
<220> FEATURE:
<223> OTHER INFORMATION: Catalytic domain of ST6Gal2

<400> SEQUENCE: 43

Arg Leu Tyr Ser Ser Met Ser Arg Ala Phe Leu Tyr Arg Leu Trp Lys
 1               5                  10                  15

Gly Asn Val Ser Ser Lys Met Leu Asn Pro Arg Leu Gln Lys Ala Met
                20                  25                  30

Lys Asp Tyr Leu Thr Ala Asn Lys His Gly Val Arg Phe Arg Gly Lys
            35                  40                  45

Arg Glu Ala Gly Leu Ser Arg Ala Gln Leu Leu Cys Gln Leu Arg Ser
        50                  55                  60

Arg Ala Arg Val Arg Thr Leu Asp Gly Thr Glu Ala Pro Phe Ser Ala
 65                  70                  75                  80

Leu Gly Trp Arg Arg Leu Val Pro Ala Val Pro Leu Ser Gln Leu His
                85                  90                  95

Pro Arg Gly Leu Arg Ser Cys Ala Val Val Met Ser Ala Gly Ala Ile
            100                 105                 110

Leu Asn Ser Ser Leu Gly Glu Glu Ile Asp Ser His Asp Ala Val Leu
        115                 120                 125

Arg Phe Asn Ser Ala Pro Thr Arg Gly Tyr Glu Lys Asp Val Gly Asn
    130                 135                 140

Lys Thr Thr Ile Arg Ile Ile Asn Ser Gln Ile Leu Thr Asn Pro Ser
145                 150                 155                 160

His His Phe Ile Asp Ser Ser Leu Tyr Lys Asp Val Ile Leu Val Ala
                165                 170                 175

Trp Asp Pro Ala Pro Tyr Ser Ala Asn Leu Asn Leu Trp Tyr Lys Lys
            180                 185                 190
```

-continued

```
Pro Asp Tyr Asn Leu Phe Thr Pro Tyr Ile Gln His Arg Gln Arg Asn
    195                 200             205

Pro Asn Gln Pro Phe Tyr Ile Leu His Pro Lys Phe Ile Trp Gln Leu
    210             215             220

Trp Asp Ile Ile Gln Glu Asn Thr Lys Glu Lys Ile Gln Pro Asn Pro
225             230             235             240

Pro Ser Ser Gly Phe Ile Gly Ile Leu Ile Met Met Ser Met Cys Arg
            245             250             255

Glu Val His Val Tyr Glu Tyr Ile Pro Ser Val Arg Gln Thr Glu Leu
        260             265             270

Cys His Tyr His Glu Leu Tyr Tyr Asp Ala Ala Cys Thr Leu Gly Ala
    275             280             285

Tyr His Pro Leu Leu Tyr Glu Lys Leu Leu Val Gln Arg Leu Asn Met
    290             295             300

Gly Thr Gln Gly Asp Leu His Arg Lys Gly Lys Val Val Leu Pro Gly
305             310             315             320

Phe Gln Ala Val His Cys Pro Ala Pro Ser Pro Val Ile Pro His Ser
                325             330             335
```

The invention claimed is:

1. A method for producing a therapeutic protein with sialylation on the at least one glycosylation site of said therapeutic protein, said method comprising the steps of:
   a) culturing a transformed mammalian cell comprising:
      i) a heterologous nucleic acid sequence (i) encoding a polypeptide comprising SEQ ID NO:35, and
      ii) at least one heterologous nucleic acid sequence (ii) encoding a therapeutic protein, the sequence of which therapeutic protein comprises at least one glycosylation site,
      so as to express the therapeutic protein with a sialylation on said at least one glycosylation site, and
   b) purifying the therapeutic protein encoded by the nucleic acid sequence (ii).

2. The method of claim 1, wherein the step b) also comprises the determination of the glycosylation pattern of the therapeutic protein.

3. The method of claim 1, wherein said method comprises the step b) of determining the glycosylation pattern of the therapeutic protein obtained in step a) and purifying the therapeutic protein with i) a sialylation on at least 2% of glycosylation site(s).

4. The method of claim 1, wherein the transformed mammalian cell is selected in the group comprising CHO cells, HEK-293 cells, COS cells, NSO cells, or SP2O cells.

5. The method of claim 1, wherein the transformed nucleic acid sequence (i) encodes a polypeptide consisting in the sequence SEQ ID NO: 35.

6. The method of claim 1, wherein the nucleic acid sequence (ii) encodes an antibody or a fragment thereof.

7. The method of claim 1, wherein the nucleic acid sequence (ii) encodes a glycoprotein hormone.

* * * * *